(12) United States Patent
Badhwar et al.

(10) Patent No.: US 11,337,799 B2
(45) Date of Patent: May 24, 2022

(54) STENTLESS BIOPOLYMER HEART VALVE REPLACEMENT CAPABLE OF LIVING TISSUE REGENERATION

(71) Applicant: University of Pittsburgh—Of the Commonwealth System of Higher Education, Pittsburgh, PA (US)

(72) Inventors: Vinay Badhwar, Washington, PA (US); Antonio D'Amore, Pittsburgh, PA (US); Yasumoto Matsumura, Pittsburgh, PA (US); William R. Wagner, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/488,002

(22) PCT Filed: Feb. 23, 2018

(86) PCT No.: PCT/US2018/019358
§ 371 (c)(1),
(2) Date: Aug. 22, 2019

(87) PCT Pub. No.: WO2018/156856
PCT Pub. Date: Aug. 30, 2018

(65) Prior Publication Data
US 2020/0054448 A1    Feb. 20, 2020

Related U.S. Application Data

(60) Provisional application No. 62/462,628, filed on Feb. 23, 2017.

(51) Int. Cl.
*A61F 2/24*    (2006.01)

(52) U.S. Cl.
CPC .............. *A61F 2/2415* (2013.01); *A61F 2/24* (2013.01); *A61F 2/2409* (2013.01);
(Continued)

(58) Field of Classification Search
CPC ........ A61F 2/2415; A61F 2/2457; A61F 2/24; A61F 2/2412; A61F 2240/005; A61F 2/2409; A61F 2230/0023
See application file for complete search history.

(56) References Cited

U.S. PATENT DOCUMENTS

| 4,902,508 A | 2/1990 | Badylak et al. |
| 4,956,178 A | 9/1990 | Badylak et al. |

(Continued)

FOREIGN PATENT DOCUMENTS

| WO | 0197741 A2 | 12/2001 |
| WO | 2013018921 A1 | 2/2013 |

(Continued)

OTHER PUBLICATIONS

Bourke et al., "Polymers derived from the amino acid L-tyrosine: polycarbonates, polyarylates and copolymers with poly(ethylene glycol)", Advanced Drug Delivery Reviews, 2003, pp. 447-466, vol. 55.

(Continued)

*Primary Examiner* — Dinah Baria
(74) *Attorney, Agent, or Firm* — The Webb Law Firm

(57) ABSTRACT

A template for a valve construct for replacement of at least one of a mitral valve and a tricuspid valve includes at least an anterior leaflet portion and at least a posterior leaflet portion, each leaflet portion having a proximal edge, a distal edge, and side edges extending between the proximal edge and the distal edge. The template further includes a plurality of substantially straight elongated chordae portions each having a proximal end connected to the distal edge of one of (Continued)

the at least two leaflet portions and a distal end extending therefrom and one or more papillary muscle head portions formed at a commissure between distal ends of at least two of the plurality of chordae portions. A total width of the leaflet portions of the template is substantially equal to a circumference of a native annulus of a heart valve.

14 Claims, 14 Drawing Sheets

(52) U.S. Cl.
CPC .......... *A61F 2/2412* (2013.01); *A61F 2/2457* (2013.01); *A61F 2230/0023* (2013.01); *A61F 2240/005* (2013.01)

(56) References Cited

U.S. PATENT DOCUMENTS

| | | |
|---|---|---|
| 5,216,115 A | 6/1993 | Kohn et al. |
| 5,281,422 A | 1/1994 | Badylak et al. |
| 5,352,463 A | 10/1994 | Badylak et al. |
| 5,372,821 A | 12/1994 | Badylak et al. |
| 5,415,667 A | 5/1995 | Frater |
| 5,509,930 A | 4/1996 | Love |
| 5,554,184 A | 9/1996 | Machiraju |
| 5,554,389 A | 9/1996 | Badylak et al. |
| 5,573,784 A | 11/1996 | Badylak et al. |
| 5,645,860 A | 7/1997 | Knapp, Jr. et al. |
| 5,711,969 A | 1/1998 | Patel et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 6,099,567 A | 8/2000 | Badylak et al. |
| 6,358,277 B1 | 3/2002 | Duran |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| RE42,857 E | 10/2011 | Cali et al. |
| 8,136,218 B2 | 3/2012 | Millwee et al. |
| 8,361,503 B2 | 1/2013 | Badylak et al. |
| 8,535,719 B2 | 9/2013 | Badylak et al. |
| 8,691,276 B2 | 4/2014 | Badylak et al. |
| 8,896,512 B2 | 11/2014 | Zebedee |
| 2002/0091441 A1 | 7/2002 | Guzik |
| 2011/0082545 A1 | 4/2011 | Freund |
| 2013/0013058 A1 | 1/2013 | Umezu et al. |
| 2014/0377213 A1 | 12/2014 | Hong et al. |
| 2018/0071087 A1 | 3/2018 | Badhwar et al. |
| 2018/0071088 A1 | 3/2018 | Badhwar et al. |

FOREIGN PATENT DOCUMENTS

| | | |
|---|---|---|
| WO | 2016138416 A1 | 9/2016 |
| WO | 2016138423 A1 | 9/2016 |

OTHER PUBLICATIONS

Fiordeliso et al., "Design, synthesis, and preliminary characterization of tyrosine-containing polyarylates: New biomaterials for medical applications", Journal of Biomaterials Science Polymer Edition, 1994, pp. 497-510, vol. 5, No. 6.

Huang et al., "A Library of L-Tyrosine-Derived Biodegradable Polyarylates for Potential Biomaterial Applications, Part 1: Synthesis, Characterization and Accelerated Hydrolytic Degradation", Journal of Biomaterials Science, 2009, pp. 935-955, vol. 20.

Hong et al., "Tailoring the degradation kinetics of poly(ester-carbonate urethane)urea thermoplastic elastomers for tissue engineering scaffolds", Biomaterials, 2010, pp. 4249-4258, vol. 31, No. 15.

Vetter et al., "Total Replacement of the Mitral Apparatus with a Stentless, Chordally Supported Mitral Valve Allograft: An Experimental Study", The Journal of Thoracic and Cardiovascular Surgery, 1996, pp. 595-604, vol. 111, No. 3.

"Total Autologous Mitral Valve Reconstruction: An Experimental Study", 2015, 2 pages, retrieved from https://www.ctsnet.org.

STENTLESS BIOPOLYMER HEART VALVE REPLACEMENT CAPABLE OF LIVING TISSUE REGENERATION

CROSS-REFERENCE TO RELATED APPLICATIONS

This application is the United States nation phase of International Application No. PCT/US2018/019358 filed Feb. 23, 2018, and claims priority to U.S. Patent Provisional Application Ser. No. 62/462,628, filed Feb. 23, 2017, each of which is hereby incorporated by reference in its entirety.

STATEMENT REGARDING FEDERAL FUNDING

This invention was made with government support under Grant No. HL068816, awarded by the National Institutes of Health. The government has certain rights in the invention.

BACKGROUND

Technical Field

The present disclosure relates to constructs and surgical methods for full or partial heart valve replacement and, in particular, to a construct formed using a template which approximates structures of a mitral or tricuspid valve, methods of forming a valve construct from the template, and surgical methods for implanting the valve construct for partial or total valve replacement.

Description of Related Art

Heart valve disease is a condition in which one or more of the valves between heart chambers of a patient malfunction. In adults, valvular heart disease continues to be a major cause of morbidity and mortality with approximately 60,000 valve replacements performed in the United States in 2013. This number does not include transcatheter aortic valve replacements (TAVR) and open surgical valve replacements. About 2,000 TAVR procedures are performed per year. About 1,000 open surgical tricuspid valve replacements are performed each year. The reported number of valve replacements in the United States also does not include mitral and tricuspid surgical repairs, which were approximately 25,000 in 2013.

Existing solutions for heart valve replacement in anatomic positions are generally limited to mechanical or bio-prosthetic prostheses. In most cases, mechanical heart valves are made entirely of synthetic materials, such as metals and pyrolytic carbon polymers. Bioprosthetic heart valves are made from tissue from animals (e.g., bovine, porcine, or equine) or from human tissue. Mechanical heart valves are very durable and may last decades. However, these valves may have limited central flow due to their designs, such as bileaflet or tilting disc mechanisms.

Valve replacement procedures can involve a partial or complete resection of native leaflets, as well as suturing a sewing ring of the replacement valve to the native valve annulus. Following such procedures, mechanical prostheses require lifelong warfarin-based anticoagulation. Existing bioprostheses are glutaraldehyde-fixed porcine or bovine valves sewn to a molded plastic stent frame covered with Dacron material. Though such bioprostheses can be managed with low dose anticoagulation or antiplatelet therapy, they often have failure modes of between 7-12 years either by primary leaflet tearing or cuspal separation at the commissures due to leaflet fatigue. Both valves are at risk of micro-thrombotic pannus formation leading to valvular or sub-valvular stenosis, a primary mode, especially for bioprostheses.

In addition to certain prefabricated valve replacement constructs, for partial valve replacements in which portions of mitral or tricuspid valves are repaired or replaced, devitalized bovine pericardium is often prepared by the surgeon. For example, a surgeon may examine the valve or valve annulus being repaired or replaced, obtain a piece of devitalized bovine pericardium, and manually size and shape the pericardium to fit with the existing valve tissue in the operating room. Success of such procedures is highly dependent upon the skill and ability of the surgeon to manually size and shape valve leaflets from the sheet of bovine pericardium.

In addition to conventional bioprostheses heart valves, several polymeric electro-spun scaffolds have been tested in vivo to provide evidence of function of such scaffolds as a heart valve leaflet surrogates. For example, the OneValve™ prosthetic heart valve is formed by a processing technique which generates a fully functioning heart valve or a biomaterial that can be crafted into a stentless heart valve. Exemplary electrospun valve constructs and methods of forming such constructs are described in International Patent Publication No. WO 2016/138416 entitled "Double Component Mandrel for Electrospun Stentless, Multi-leaflet Valve Fabrication" and International Patent Publication No. WO 2016/138423 entitled "Retrievable Self-expanding Non-thrombogenic Low-profile Percutaneous Atrioventricular Valve Prosthesis," each of which is incorporated by reference in its entirety. While the stentless OneValve™ platform can be applied to all anatomic valve positions (aortic, pulmonic, mitral, and tricuspid), there is a pressing need for constructs specifically for atrio-ventricular (AV) valve positions (e.g., for mitral and tricuspid positions). However, processing biomaterials into heart valve leaflet shapes is more complex in the mitral and tricuspid positions, where valve leaflets are attached to the ventricular walls through the chordae tendineae and to the papillary muscles at commissures between adjacent chordae.

In view of such problems, there is a need for an improved valve construct for AV valve positions which can be implanted with or without reduced reliance on anticoagulation therapies. A method for preparing and surgically implanting such a valve would also be required.

SUMMARY

In view of the difficulties caused by conventional valve replacement surgical procedures, an improved valve construct and associated surgical method are needed. The template, valve construct, and methods disclosed herein are designed to address these issues.

According to an aspect of the disclosure, a template for a valve construct for replacement of at least one of a mitral valve and a tricuspid valve comprises: at least an anterior leaflet portion and at least a posterior leaflet portion, each leaflet portion comprising a proximal edge, a distal edge, and side edges extending between the proximal edge and the distal edge. The template further comprises a plurality of substantially straight elongated chordae portions each having a proximal end connected to the distal edge of one of the at least two leaflet portions and a distal end extending therefrom and one or more papillary muscle head portions formed at a commissure between distal ends of at least two of the plurality of chordae portions. A total width of the leaflet portions of the template is substantially equal to a circumference of a native annulus of a heart valve.

According to another aspect of the disclosure, a valve construct formed according to a cutting guide comprises a flat sheet formed from a natural or synthetic biocompatible material. The sheet comprises at least an anterior leaflet portion and at least a posterior leaflet portion, each leaflet portion comprising a proximal edge, a distal edge, and side edges extending between the proximal edge and the distal edge. The sheet further comprises a plurality of substantially straight elongated chordae portions each having a proximal end connected to the distal edge of one of the at least two leaflet portions and a distal end extending therefrom and one or more papillary muscle head portions formed at a commissure between distal ends of at least two of the plurality of chordae portions. A total width of the leaflet portions of the template is substantially equal to a circumference of a native annulus of a heart valve.

According to another aspect of the disclosure, a method of forming an implantable valve construct comprises: providing a substantially flat substrate of a natural or synthetic biocompatible material and cutting a shape from the substantially flat sheet as directed by a cutting guide to form the valve construct. The shape can comprise at least an anterior leaflet portion and at least a posterior leaflet portion, each leaflet portion comprising a proximal edge, a distal edge, and side edges extending between the proximal edge and the distal edge. The sheet can further comprise a plurality of substantially straight elongated chordae portions each having a proximal end connected to the distal edge of one of the at least two leaflet portions and a distal end extending therefrom and one or more papillary muscle head portions formed at a commissure between distal ends of at least two of the plurality of chordae portions. A total width of the leaflet portions of the template can be substantially equal to a circumference of a native annulus of a heart valve.

According to another aspect of the disclosure, a method for performing a valve repair or valve replacement procedure by implanting a natural or synthetic valve construct to a valve annulus of a patient comprises: dissecting at least one of a mitral or tricuspid valve of the patient to reveal structures of the valve annulus; attaching a portion of the valve construct to the valve annulus by suturing a free proximal edge of the valve construct to the valve annulus; attaching muscle head portions of the valve construct to papillary muscles of a ventricle of the patient; and connecting side edges of the construct together to form an enclosed ring. The valve construct can comprise: at least an anterior leaflet portion and at least a posterior leaflet portion, each leaflet portion comprising a proximal edge, a distal edge, and side edges extending between the proximal edge and the distal edge. The valve construct can further comprise a plurality of substantially straight elongated chordae portions each having a proximal end connected to the distal edge of one of the at least two leaflet portions and a distal end extending therefrom and one or more of the papillary muscle head portions formed at a commissure between distal ends of at least two of the plurality of chordae portions. A total width of the leaflet portions of the valve construct can be substantially equal to a circumference of a native annulus of a heart valve.

According to another aspect, a method of forming an implantable valve construct comprises forming a substrate of a natural or synthetic biocompatible material into a predetermined shape to form the valve construct. In some examples, the predetermined shape comprises at least an anterior leaflet portion and at least a posterior leaflet portion, each leaflet portion comprising a proximal edge, a distal edge, and side edges extending between the proximal edge and the distal edge. The predetermined shape can further comprise a plurality of substantially straight elongated chordae portions each having a proximal end connected to the distal edge of one of the at least two leaflet portions and a distal end extending therefrom and one or more papillary muscle head portions formed at a commissure between distal ends of at least two of the plurality of chordae portions. A total width of the leaflet portions of the template can be substantially equal to a circumference of a native annulus of a heart valve.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DETAILED DESCRIPTION

Figure 1:
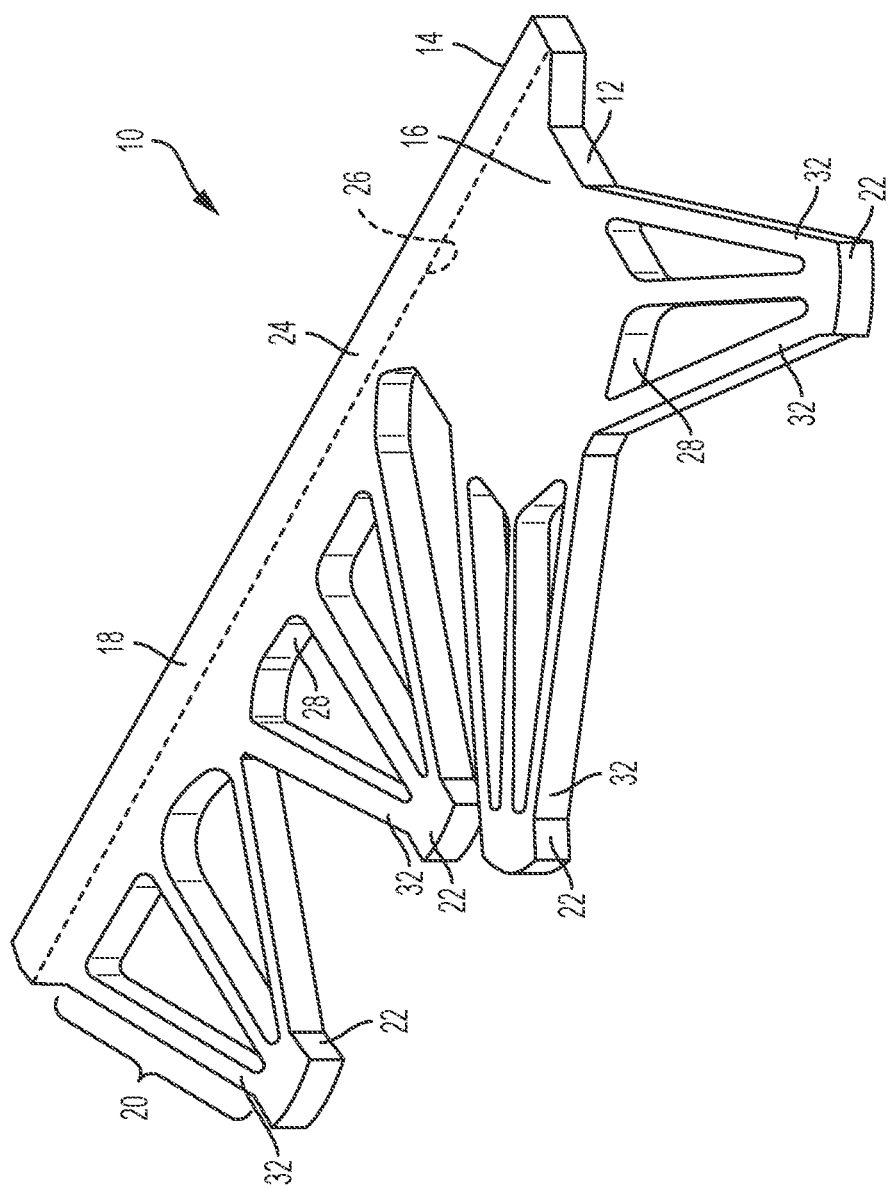
FIG. 1 is a perspective view of a template for a heart valve construct for replacement or repair of a mitral valve according to an aspect of the disclosure.

As used herein, the singular form of "a", "an", and "the" include plural referents unless the context clearly dictates otherwise.

As used herein, the terms "upper", "lower", "right", "left", "vertical", "horizontal", "top", "bottom", "lateral", "longitudinal", and derivatives thereof, shall relate to the invention as it is oriented in the drawing figures. The term "proximal" can refer to a portion of a structure nearest to the center of the structure or to a point of attachment or actuation of the structure. As such, a "proximal portion" of a construct formed from a valve template refers to a portion of the valve construct configured to be attached to a valve annulus. The term "distal" refers to a portion of a structure farthest away from the center or from the point of attachment or actuation of the structure (e.g., the portion of the structure opposite from the proximal portion). As such, a "distal portion" of a valve construct formed from a valve template can refer to a portion of the valve construct farthest away from the portion which is attached to the valve annulus. In general, a distal portion of the valve construct can include papillary muscle head portions which extend from leaflet portions of the valve construct. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Unless indicated to the contrary, the numerical parameters set forth in the following specification and attached claims are approximations that can vary depending upon the desired properties sought to be obtained by the present disclosure. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the "treatment" or "treating" of a condition, wound, or defect means administration to a patient by any suitable dosage regimen, procedure, and/or administration route of a composition, device, or structure with the object of achieving a desirable clinical/medical end-point, including repair and/or replacement of a tricuspid or mitral valve.

As used herein, the term "patient" or "subject" refers to members of the animal kingdom including but not limited to human beings and "mammal" refers to all mammals, including, but not limited to human beings.

A polymer composition is "biocompatible" in that the polymer and, where applicable, degradation products thereof, are substantially non-toxic to cells or organisms within acceptable tolerances, including substantially non-carcinogenic and substantially non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers, and can be both natural and/or synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer (monomer residue) that the polymer comprises is not the same as the monomer prior to incorporation into a polymer, in that at the very least, certain groups are missing and/or modified when incorporated into the polymer backbone. A polymer is said to comprise a specific type of linkage if that linkage is present in the polymer.

As described herein, a "fiber" is an elongated, slender, thread-like, and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic.

By "biodegradable or "bioerodable," it is meant that a polymer, once implanted and placed in contact with bodily fluids and tissues, will degrade either partially or completely through chemical reactions with the bodily fluids and/or tissues, typically and often preferably over a time period of hours, days, weeks, or months. Non-limiting examples of such chemical reactions include acid/base reactions, hydrolysis reactions, and enzymatic cleavage. The biodegradation rate of the polymer matrix may be manipulated, optimized, or otherwise adjusted, so that the matrix degrades over a useful time period. The polymer or polymers typically will be selected so that it degrades in situ over a time period to optimize mechanical conditioning of the tissue. For instance, in the case of abdominal wall repair, it is desirable that the matrix dissolves over at least a week and preferably longer. More importantly, the matrix would have to retain its supportive capacity until tissue remodeling occurs, such as for at least 2-8 weeks, or longer.

According to an aspect of the disclosure, a porous biocompatible, biodegradable, fibrous, biomaterial construct is disclosed herein which provides durable in situ functioning of a native valve. The valve construct generally includes a distal sewing end for surgical fixation to both papillary muscle heads, a proximal sewing end in the form of a biodegradable sewing ring of biopolymer for facilitation to the native valve annulus, and a final sewing margin (e.g., a side edge) that permits sewing the two ends of the graft to complete the valve implantation. Desirably, when implanted, the valve construct is slowly replaced by endogenous tissue growth of endothelial cells and native tissue. The construct disclosed herein retains its form and function during use and addresses elements of heart valve replacement, namely durability and non-thrombogenicity, through natural biomechanics.

In addition to being used to produce tissue engineered scaffolds designed to achieve endogenous tissue growth, according to other aspects of the disclosure, the cutting template disclosed herein can be adopted for use with other synthetic or biologically derived materials regardless of the processing method.

In some examples, a number of standard size (e.g., small, medium, and large) valve constructs are made available to a surgeon during the valve replacement or repair procedure. For example, a number of pre-fabricated valve constructs may be made available to the surgeon in the form of a kit. The surgeon selects an appropriate valve construct from the kit based on patient size and on the type of procedure being performed. In some examples, the surgeon then manually shapes or sizes the selected valve construct prior to implantation. In some examples, the valve construct includes all leaflets of a valve. In other examples, a valve construct may include only a single leaflet. In that case, a surgeon may use multiple valve constructs during a valve repair procedure to repair a single valve.

In some examples, the valve construct and surgical methods disclosed herein address challenges of adapting a valve construct for use in AV positions. For example, the valve construct disclosed herein is formed with a simplified cutting geometry for the mitral and tricuspid positions. The valve construct includes shapes and structures representative of both valve leaflets and chordae tendineae. This approach enables a naturally functioning replacement while preserving papillary muscle and ventricular continuity to the mitral annulus. This configuration also enables tripartite tissue in-growth from the annulus, papillary muscle, and circulatory endothelial deposition.

It is believed that in developed nations the valve construct disclosed herein may have a major impact on routine AV valve replacement for patients requiring a durable solution without oral Warfarin therapy (blood thinner). In developing nations, the valve construct disclosed herein may also beneficially provide an easy to implant solution for the global issue of premature rheumatic AV valve stenosis.

Exemplary Template for Heart Valve Construct

Figure 2:
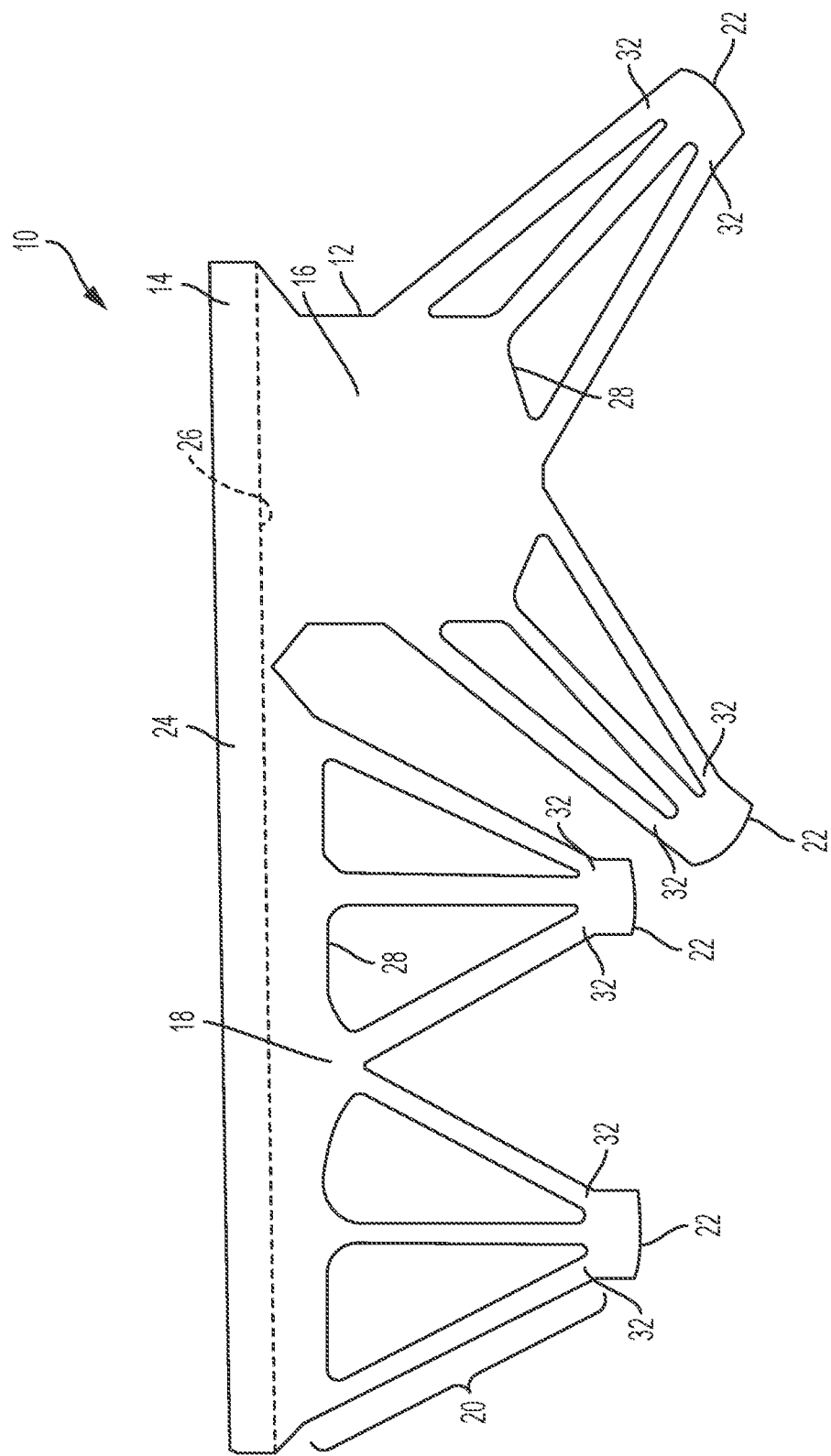
FIG. 2 is a top view of the template of FIG. 1.
Figure 3:
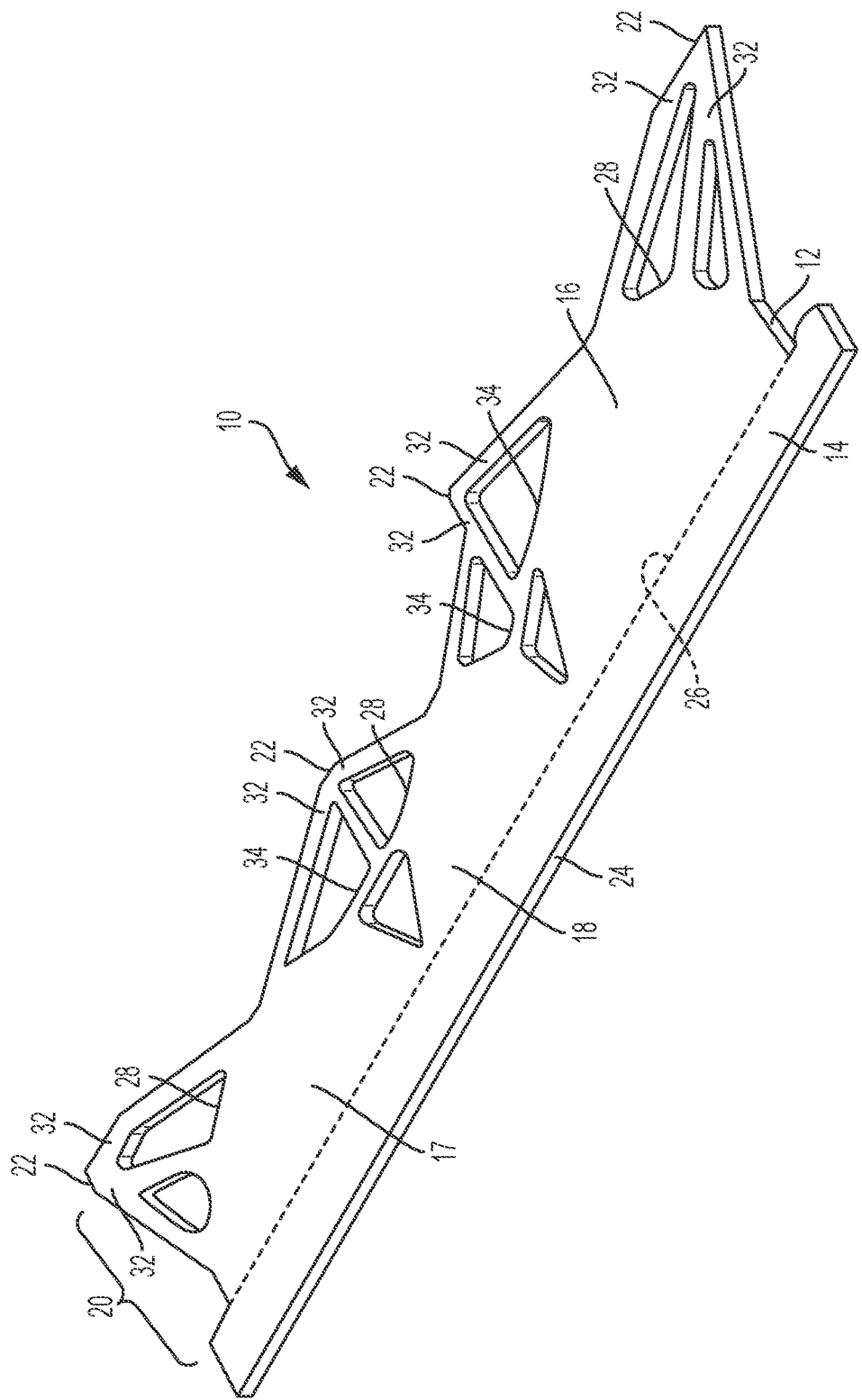
FIG. 3 is a perspective view of a template for a heart valve construct for replacement or repair of a tricuspid valve according to an aspect of the disclosure.
Figure 4A:
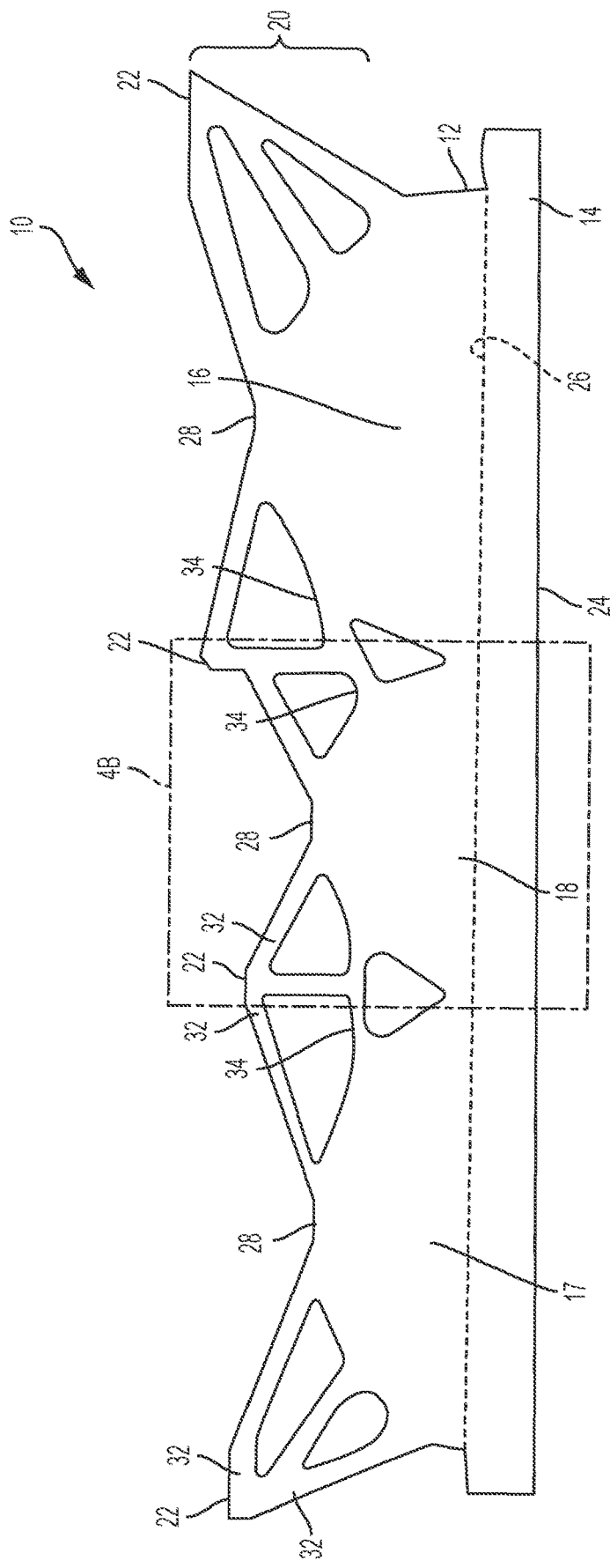
FIG. 4A is a top view of the template of FIG. 3.
Figure 4B:
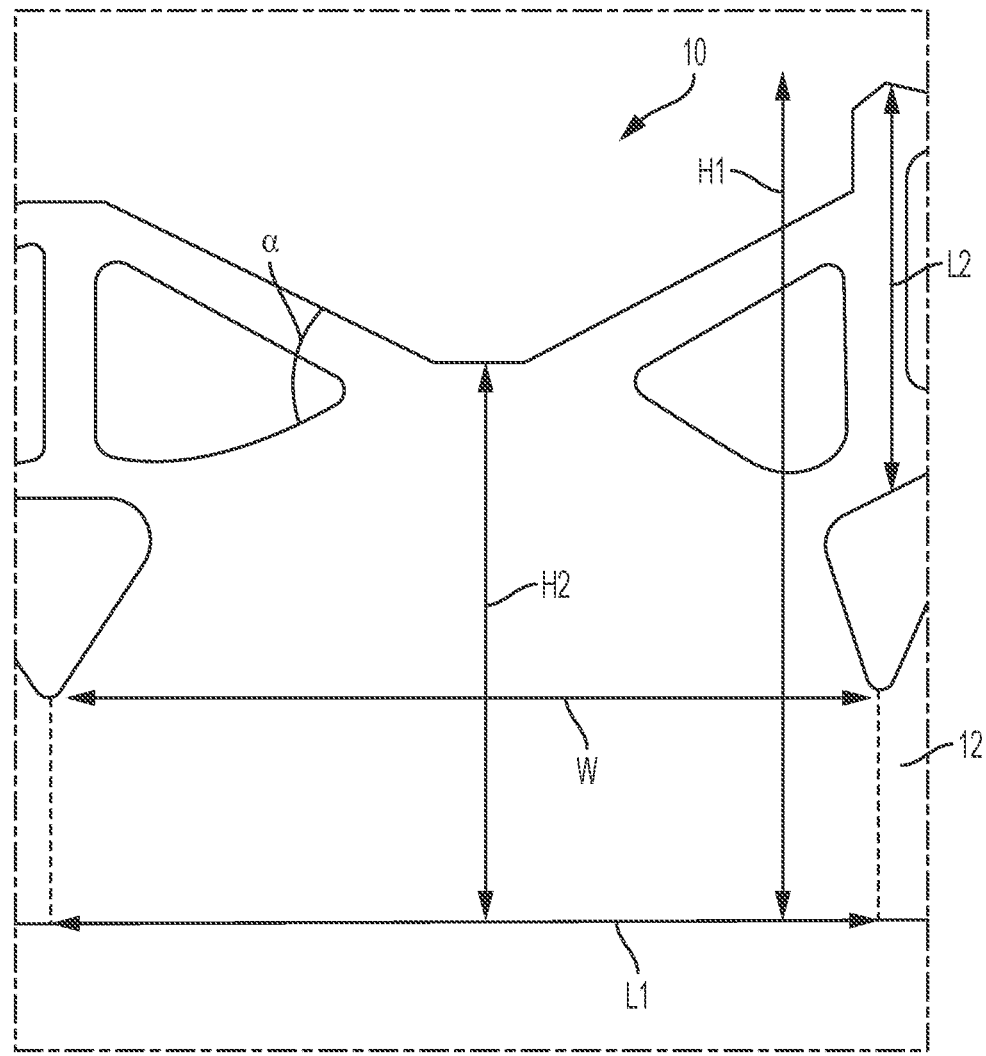
FIG. 4B is an enlarged view of a portion of the top view of FIG. 4A enclosed by shape 4B.
Figure 5A:
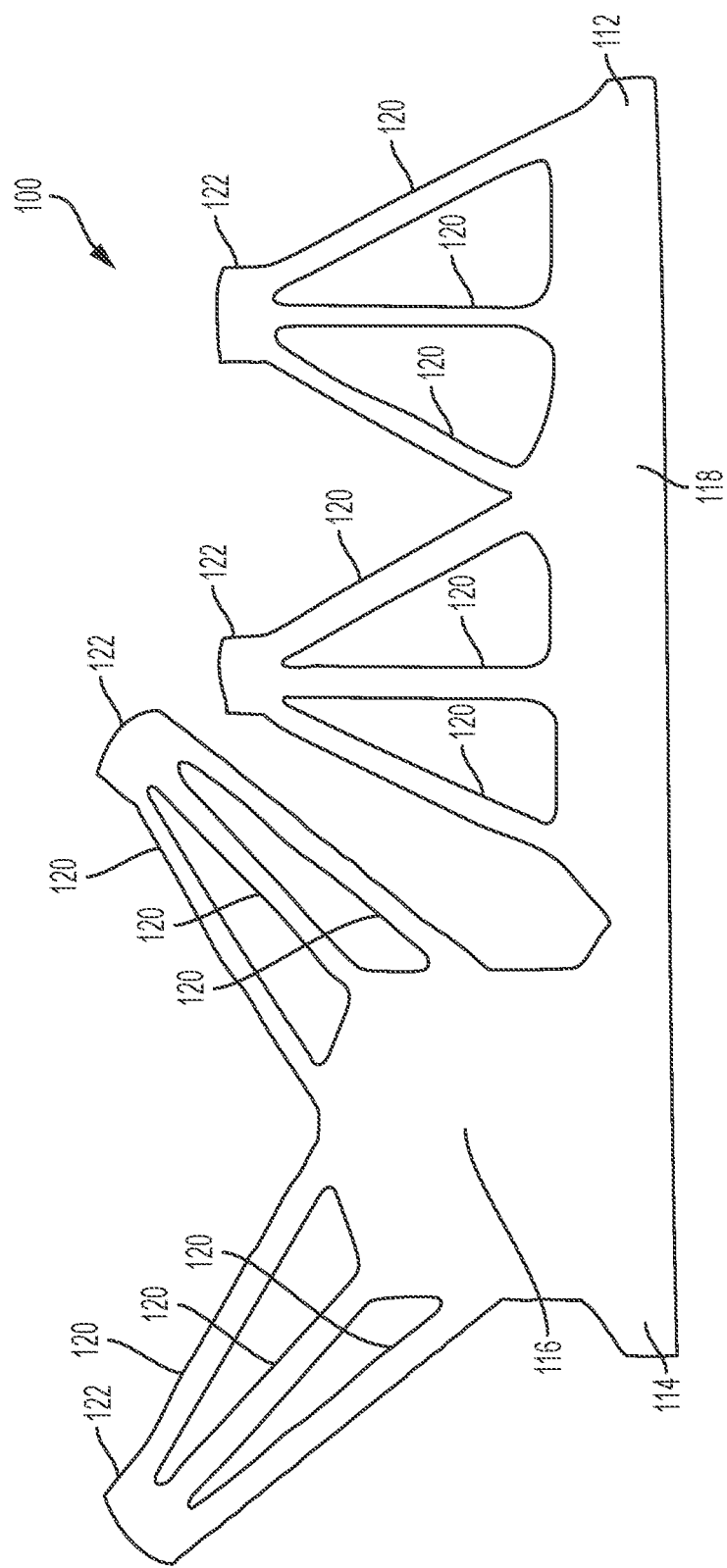
FIGS. 5A and 5B are top views of embodiments of valve constructs according to aspects of the disclosure.
Figure 5B:
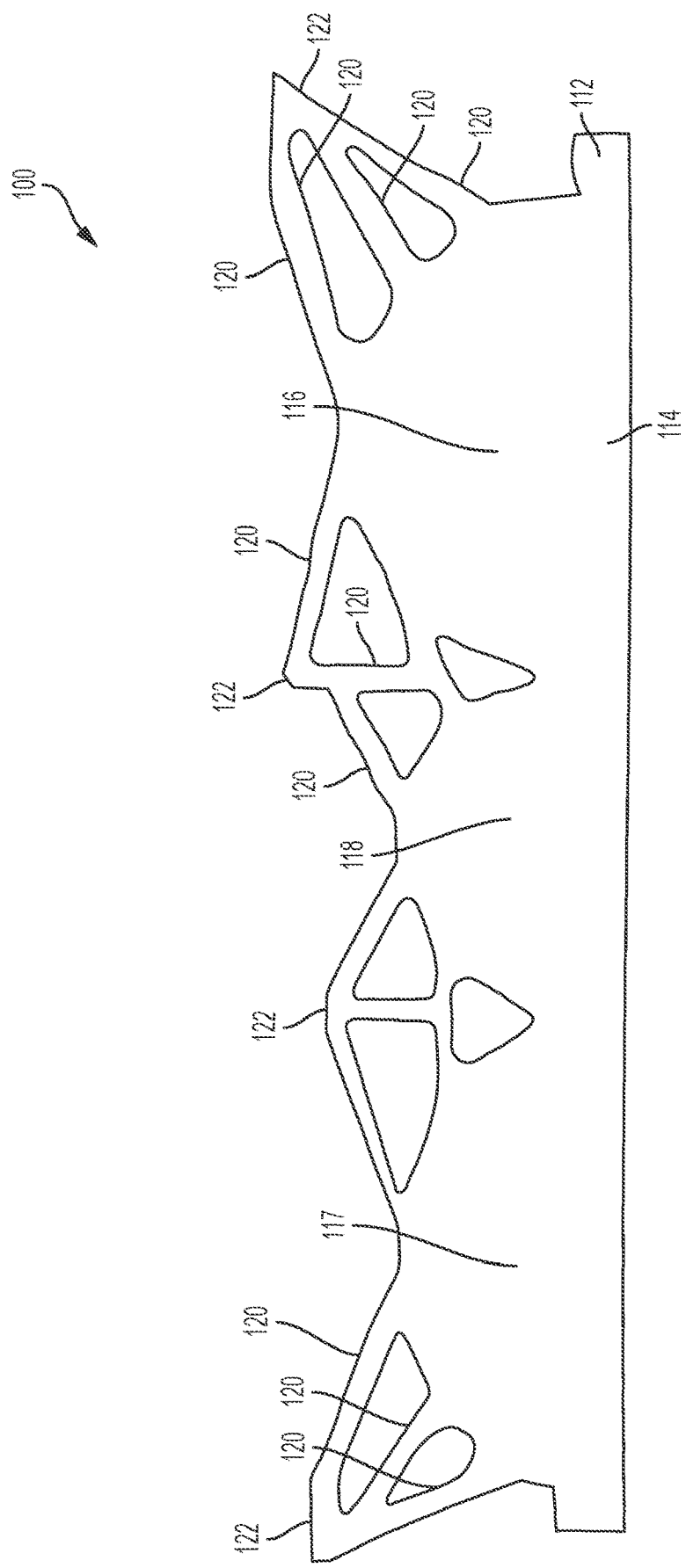

With reference to FIGS. 1-4A, a template 10 for forming a valve construct 100 (shown in FIGS. 5A, 5B, and 12A-14B) for use in valve repair and replacement procedures is provided. In some examples, as shown in FIGS. 1 and 2, the template 10 is configured to form a valve construct for a mitral valve. In other examples, as shown in FIGS. 3-4B, the template is configured to form a construct for use in the tricuspid valve position. Exemplary valve constructs 100 implanted ex vivo are shown in the photographs of FIGS. 12A-14B. In general, when laid flat, prior to implantation, the valve construct 100 has a shape identical to the template used to form the valve construct 100.

As shown in FIGS. 1-4B, the template 10 is formed from a substantially flat sheet 12, such as a metal, ceramic, or rigid plastic sheet. The template 10 can be formed by any suitable fabrication technique including three-dimensional printing techniques, computer-controlled cutting machinery, laser cutting techniques, and others. In some examples, the template 10 is formed using 0.8 mm thick stainless steel stock cut using a laser cutter platform. In order to control the laser cutter platform, a computer numerical control code (CNC) prepared from a template drawing file can be downloaded to a machine controller of the laser cutter. The laser cutter can be orientated at a start point (e.g., a X, Y, Z location). Laser optics of the cutter and CNC code control and direct a $CO_2$ laser beam to follow the CNC pattern from the start point to burn away the stainless steel material producing the desired template layout.

Valve Template Portions and Configuration

With continued reference to FIGS. 1-4B, the geometry and configuration of the template 10 will now be described in detail. As discussed herein, the geometry and configuration of the template 10 is selected to approximate and resemble anatomical features of a human heart valve with simplified structural features to permit easier cutting and implantation. As will be appreciated by one of ordinary skill in the art, the template size and shape may be scaled up or down based on sizing requirements for a particular patient. Generally, it is believed that the size of a native heart valve for an individual can be estimated based on an individual's body surface area (BSA) or height. Typical replacement valves have a diameter of about 30 to 34 mm in the mitral position and about 32-36 mm in the tricuspid position.

As shown in FIGS. 1-4A, the template 10 includes: at least two leaflet portions, such as an anterior leaflet portion 16, a septal leaflet portion 17, and a posterior leaflet portion 18, a plurality of chordae tendineae portions 20, and one or more capillary muscle head portions 22. Generally, a maximum total width of the at least two leaflet portions, such as the anterior leaflet portion 16, the septal leaflet portion 17, and the posterior leaflet portion 18, substantially corresponds to a length of a circumference of a native annulus of a heart valve. In some examples, the template 10 also includes a sewing ring portion 14 extends along a proximal longitudinal free edge 24 of the template sheet 12. A length of the sewing ring portion 14 is similar to the total width of the leaflet portions and, accordingly, the sewing ring 14 also has a length suitable for attachment about the circumference of the native annulus of the heart valve. In some examples, the sewing ring portion 14 has a longitudinal length of about 7 to 11 cm In some examples, the leaflet portions 16, 17, 18 include a substantially straight proximal side 26 co-extensive with a distal end of the sewing ring portion 14 and a free distal edge 28 extending a distance from the sewing ring portion 14. Desirably, the leaflet portions 16, 17, 18 have a height of between about 22 mm and 27 mm. The distal edge 28 can be a curved edge or can be formed from a plurality of connected substantially straight segments. Substantially straight edges may be easier for the surgeon to cut using a scalpel and, as such, may be preferable for many applications. In other examples, as described in connection with FIGS. 8A-9C, leaflet portion(s) 16, 17, 18 can be separate structures for creating different portions of the valve construct.

In some examples, the chordae portions 20 each have a proximal end 30 connected to the distal edge 28 of one of the leaf portions 16, 17, 18 and a distal end 32 extending therefrom. As discussed herein, length and width of the chordae portions is selected to approximate or resemble chordae tendineae of a normal (e.g., statistically average) patient. Further, as discussed herein, in some examples, different sizes of templates 10 (e.g., small, medium, and large) can be provided with chordae portions 20 sized for different groups of patients. In some examples, the chordae portions 20 are substantially straight segments having a length of about 16 mm to 22 mm and a width of about 2 mm In some examples, the one or more papillary muscle head portions 22 are formed at a commissure between distal ends 32 of at least two of the chordae portions 20. Further, in a preferred example, the papillary muscle head portions 22 are formed at a commissure between distal ends 32 of three chordae portions extending from the same leaflet. The head portions 22 form the distal sewing end of the valve construct 100 configured to be connected to the papillary muscle heads of the valve annulus. In addition to the distally extending chordae portions 20, in some examples, the template 10 also includes one or more transverse chordae portions 34 extending between adjacent leaflet portions, as shown in FIGS. 3 and 4A.

The relative dimensions of structures of the template 10 are determined with respect to corresponding structures of a native heart valve. However, as discussed herein, there is a variability in leaflet size, chordae position, and number of chordae between subjects, based on body size. Further, structures such as the chordae control the stresses experienced by the valves. As such, having an understanding of the optimum size, location, and number is needed to optimize valve construct performance and longevity.

As shown in FIG. 4B, the template 10 can be defined by one or more of the following geometric parameters: (i) free edge length L1; (ii) total height of the leaflet and chordae H1; (iii) leaflet height H2; (iv) length of chordae L2; (v) chordae angle $\alpha$ from the leaflet; and (vi) leaflet width W for each valve and leaflet. Suitable parameter values for the template 10 and routines for determining such parameter values will now be described.

Mitral Valve Dimensions

In order to determine sizes for structural features of the template 10, various assumptions about relative sizing of different valve structures were used. For example, in the case of the mitral valve, the inventors assumed that the valve was square and that the valve annulus was a circumscribed circle of the valve. The height of the posterior leaflet portion 18 was assumed to be a valve "A." The width of the anterior leaflet portion 18 was 7A. For the anterior leaflet portion 16, the width was assumed to be 3A. Both anterolateral and posterolateral commissure were given a dimension of 1A. A total length of circumference was determined to be 12A (3A+7A+1A×2). As such, the diameter of the valve was determined to be about 4A (12A/$\pi$). The chordae tendineae were assumed to be ⅔ length of the anterior leaflet height, so that the length of chordae tendineae was 2A. The chordae width was selected to be 2 mm.

Based upon these geometric relationships between structures of the mitral valve, a valve template and construct for a patient of normal size has the following parameter values. For a mitral valve, the free edge or sewing ring length is about 105 mm (anterior leaflet portion 16 has a length of about 25 mm and the posterior leaflet portion 18 has a length of about 80 mm), total height (with chordae) of about 30 mm, leaflet height of about 27 mm, length of chordae of about 18-22 mm, chordae angle of 90°, and leaflet width of about 24 mm. The posterior leaflet has a total height (with chordae) of about 32 mm, a leaflet height of 7 mm, a length of chordae of about 16-20 mm, and chordae angle of 40-70°.

Tricuspid Valve Dimensions

For the tricuspid valve, the following assumptions were made for dimensional relationships between valve structures. The width of the anterior leaflet 16 was assumed to be 7A and the height was 4A. The width of the posterior leaflet 18 was assumed to be 5A and the height was 3A. The width of the septal leaflet was assumed to be 7A and the height was assumed to be 3A. The circumference of the annulus and length of the proximal free edge of the valve construct was determined to be 19A (7A+5A+7A). The diameter of the valve was determined to be about 6A (19A/$\pi$) In this configuration, since both anterior and posterior papillary muscles are near the anteroposterior or posteroseptal commissure, some chordae tendineae attached to the anteroposterior commissure side of the leaflet anchor directly to the right ventricle wall and not to the papillary muscles. Because of difficulty and unstableness of suturing artificial chordae to the ventricle wall, it was determined that the length of chordae tendineae was 3A for most of the chordae. An additional 1A was added to the chordae near the anteroposterior commissure side to reach the papillary muscle. As with the mitral valve, the chordae width is about 2 mm.

Based on the geometric relationships for structures of the tricuspid valve, exemplary dimensions for the tricuspid valve for a normal sized individual are as follows. The total length of the free edge of the valve or template is about 99 mm (37 mm for the anterior and septal leaflets portions 16, 17, and 25 mm for the posterior leaflet portion 18). For the anterior leaflet portion 16, the total height (with chordae) is about 35 mm, the leaflet height is about 22 mm, the length of the chordae is about 10 mm to 13 mm (anterior-posterior side) and 15 mm to 18 mm (anterior-septal side), the chordae angle is about 45-90°, and the leaflet width is about 30 mm. For the tricuspid septal leaflet portion 17, the total height (with chordae) is about 40 mm, the leaflet height is about 17 mm, the length of chordae is about 12 mm to 14 mm (posterior-septal side) and 16 mm to 20 mm (anterior-septal side), the chordae angle is about 45-90°, and the leaflet width is about 30 mm. The posterior leaflet portion 18 has a total height (with chordae) of about 25 mm, the leaflet height is about 17 mm, the length of chordae is about 10 mm to 13 mm (anterior-posterior side) and 12 mm to 14 mm (posterior-septal side), the chordae angle of 45-90°, and the leaflet width of 22 mm.

Exemplary Valve Construct

According to another aspect of the disclosure, a valve construct 100 (shown in FIGS. 5A, 5B, and 12A-14B) produced based from one of the above-described templates will now be described. The valve construct 100 is formed from a substantially flat sheet 112 of flexible natural or synthetic material. The valve construct 100 is substantially identical in shape to the template used for forming the construct and comprises, for example, a sewing ring portion 114, at least two leaflet portions, such as an anterior leaflet portion 116, a septal leaflet portion 117, and/or a posterior leaflet portion 118, a plurality of chordae tendineae portions 120 extending from a distal edge of the leaflet portions 116, 117, 118, and one or more capillary muscle head portions 122. Specifically, a mitral valve construct (shown in FIG. 5A) includes an anterior leaflet portion 116 and an elongated posterior leaflet portion 118. A construct 100 for a tricuspid valve (shown in FIG. 5B) comprises three leaflet portions having about the same width, specifically, the anterior leaflet portion 116, septal leaflet portion 117, and posterior leaflet portion 118. The sewing ring portion 114 is configured to be connected about the circumference of the valve annulus. The muscle head portions 122 of the construct 100, which are located at commissures of two or more adjacent chordae portions 120, are configured to be connected to papillary muscles of a ventricle in a suitable manner, as is known in the art.

The sheet 112 of the valve construct 100 can be formed from a variety of different types of natural or synthetic materials depending on the therapeutic needs of particular patients. In some examples, the valve construct is formed from natural fibrous sheets, such as sheets of extra-cellular matrix materials ("ECM material") derived from, for example, bovine pericardium tissue. In other examples, the construct 100 is formed from a synthetic biodegradable material in the form of a tissue scaffolds for promoting cell growth in the implanted valve structure.

"ECM material" is a material prepared from an extracellular matrix-containing tissue including, for example, decellularized or devitalized tissues. ECM material can be used to produce gels or fibrous sheets according to the methods, compositions, and devices described in the following patents: U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; 6,893,666; 8,361,503; and 8,691,276.

In certain examples, ECM material is decellularized tissue prepared from tissue of a vertebrate animal, for example and without limitation, from a mammal, including, but not limited to, human, monkey, pig, cow, and sheep. The ECM material can be prepared from any organ or tissue, including without limitation, urinary bladder, intestine, liver, esophagus, heart, and dermis. The ECM material may or may not include the basement membrane portion of the tissue. In certain examples, the ECM material includes at least a portion of the basement membrane. In certain examples, the ECM material is prepared from pericardium or valve leaflets obtained, for example, from a pig, cow, horse, monkey, or human, for example bovine pericardium or porcine valve leaflets.

ECM material can be decellularized, devitalized, disinfected, sterilized, and/or dried by any useful method as are broadly known in the art, typically employing enzymatic digests, for example, with trypsin, surfactant, or detergent treatment, and use of solvents, buffers, and washes, as adapted to any given tissue type. The ECM material can be sterilized by any of a number of methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be cross-linked, e.g., with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide, dehydrothermal, or photooxidation methods. More typically, ECM is disinfected by immersion in 0.1% (v/v) peracetic acid ($\sigma$), 4% (v/v) ethanol, and 96% (v/v) sterile water for 2 h. The decellularized tissue is then washed twice for 15 min with PBS (pH=7.4) and twice for 15 min with deionized water.

Commercially available ECM materials derived, e.g., from small intestinal submucosa or SIS include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another example, the ECM material is derived from dermis. Commercially available preparations include, but are not limited to, Pelvicol™ (crosslinked porcine dermal collagen, sold as Permacol™ in Europe; Bard Medical Division, Covington, Ga.), Repliform™ (Microvasive; Boston, Mass.) and Alloderm™ (LifeCell; Branchburg, N.J.). In another example, the ECM is derived from urinary bladder. Commercially available preparations include, but are not limited to, UBM (Acell Corporation; Jessup, Md.).

Synthetic polymer materials can also be used for valve constructs. As used herein, the term "polymer" refers to both synthetic polymeric components and biological polymeric components. "Biological polymer(s)" are polymers that are obtained from biological sources, such as, without limitation, mammalian or vertebrate tissue, as in the case of certain ECM-derived compositions. Biological polymers can be modified by additional processing steps. "Synthetic polymer(s)" are man-made. Polymer(s), in general include, without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s). Polymer(s) are formed into any useful form such as, without limitation, a hydrogel, a porous mesh, a fiber, woven mesh, or non-woven mesh, such as, for example and without limitation, a non-woven mesh formed by electrodeposition, e.g., by electrospinning, using electrostatic deposition of polymer solutions or melts. For example, a substrate for the valve construct 100 may be formed by electrospinning polymer fibers onto a collector that can be flat or can be a spinning mandrel, to form a fibrous mesh. After formation using a rotating mandrel, the mesh may be cut from the mandrel and sized to form a substantially flat sheet to be cut or dissected to a desired shape. Electrodeposition can be isotropic (non-aligned fiber deposition) or anisotropic (aligned fiber deposition), or both, with portions of the structure being isotropic, and other portions being anisotropic. Methods of controlling electrodeposition of polymers to produce isotropic and anisotropic, even constructs containing two or more anisotropic portions with different alignments/orientations, are broadly-known, e.g., by manipulating rotation of the mandrel, and positioning of the mandrel or collector relative to the polymer sources (e.g., spinnerettes, needles, spinning tips, etc.), using computer-implemented methods, xyz stages, and other robotics as are broadly-known and readily implemented.

In further detail according to some examples, the properties of electrospun materials can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other embodiments, the biased target is moved randomly relative to the orifice, so that the resistance to strain in the plane of the non-woven mesh is isotropic. The target can also be a rotating mandrel. In this case, the properties of the non-woven mesh may be changed by varying the speed of rotation. The properties of the electrospun elastomeric scaffold may also be varied by changing the magnitude of the voltages applied to the electrospinning system. In one particularly preferred embodiment, the electrospinning apparatus includes an orifice biased to 12 kV, a target biased to −7 kV, and a focusing ring biased to 3 kV. Moreover, a useful orifice diameter is 0.047" (I.D.) and a useful target distance is about 23 cm. A useful range of high-voltage to be applied to a polymer suspension or melt is from 0.5-30 kV, more preferably 5-25 kV, even more preferably 10-15 kV.

In some aspects, the valve construct 100 is formed from a biodegradable and biocompatible polymer composition. Generally, the polymeric compositions suitable for the structures described herein are any polymer that is biocompatible and can be biodegradable. In certain non-limiting examples, the biodegradable polymers comprise homopolymers, copolymers, and/or polymeric blends comprising, without limitation, one or more of the following monomers: glycolide, lactide, caprolactone, dioxanone, and trimethylene carbonate. In other non-limiting examples, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain polypeptides or biomacromolecules as building blocks which are susceptible to chemical reactions once placed in situ. In one non-limiting example, the polymer composition comprises a polypeptide comprising the amino acid sequence alanine-alanine-lysine, which confers enzymatic lability to the polymer. In another non-limiting examples, the polymer composition comprises a biomacromolecular component derived from an ECM. For example, the polymer composition may comprise the biomacromolecule collagen so that collagenase, which is present in situ, can degrade the collagen. The polymers used herein may be elastomeric, meaning they change shape on application of a deforming force and substantially return to an original shape when the deforming force is removed.

In another non-limiting example, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

A number of biocompatible, biodegradable elastomeric (co)polymers are known and have been established as useful in preparing cell growth matrices, including biodegradable poly(ester urethane) urea (PEUU), poly(ether ester urethane) urea (PEEUU), poly(ester carbonate)urethane urea (PECUU), and poly(carbonate)urethane urea (PCUU). In general, useful (co)polymers comprise monomers derived from alpha-hydroxy acids including polylactide, poly(lactide-co-glycolide), poly(L-lactide-co-caprolactone), polyglycolic acid, poly(dl-lactide-co-glycolide), and poly(1-lactide-co-dl-lactide); monomers derived from esters including polyhydroxybutyrate, polyhydroxyvalerate, polydioxanone, and polygalactin; monomers derived from lactones including polycaprolactone; monomers derived from carbonates including polycarbonate, polyglyconate, poly(glycolide-co-trimethylene carbonate), and poly(glycolide-co-trimethylene carbonate-co-dioxanone); monomers joined through urethane linkages, including polyurethane, and poly(ester urethane) urea elastomer.

The biodegradable polymers are, for example and without limitation, homopolymers, copolymers, and/or polymeric blends. In certain examples, the polymer(s) comprise, without limitation, one or more of the following monomers: glycolide, lactide, caprolactone, dioxanone, and trimethylene carbonate. According to certain examples, the polymer is chosen from one or more of: a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(1-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polymer comprising urethane linkages, a polyurethane, a poly(ester urethane) urea, a poly(ester urethane) urea elastomer, a poly(ester carbonate urethane) urea, a poly(carbonate urethane) urea, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid, and gelatin. In one example, the polymer composition comprises a poly(ester urethane) urea with from about 25% wt. to about 75% wt. collagen. In another example, the polymer composition comprises elastin, collagen, or a mixture thereof, for example and without limitation, from about 25% wt. to about 75% wt. of a mixture of collagen and elastin, which are in approximately (about) equal amounts. In yet another example, the polymer comprises a polycaprolactone. In yet another example, the polymer comprises a polycaprolactone diol. In yet another example, the polymer comprises a triblock copolymer comprising polycaprolactone, poly(ethylene glycol), and polycaprolactone blocks.

In some examples, the valve construct 100 may be formed from a biodegradable and biocompatible scaffold material, such as a synthetic polymeric composition comprising poly(ester-urethane)urea (PEUU). PEUU can be synthesized using putrescine as a chain extender and a two-step solvent synthesis method. For example, a poly(ester urethane) urea elastomer (PEUU) may be made from polycaprolactonediol (MW 2,000) and 1,4-diisocyanatobutane, with a diamine, such as putrescine as the chain extender. A suitable PEUU polymer may be made by a two-step polymerization process whereby polycaprolactone diol (Mw 2,000), 1,4-diisocyanatobutane, and putrescine are combined in a 1:2:1 molar ratio though virtually any molar feed ratio may suffice so long as the molar ratio of each monomer component is >0. In one embodiment, the molar feed ratio of polycaprolactone diol plus putrescine is equal to that of diisocyanatobutane. In the first polymerization step, a 15 wt % solution of 1,4-diisocyanatobutane in DMSO is stirred continuously with a 25 wt % solution of diol in DMSO. In the second step, stannous octoate is added and the mixture is allowed to react at 75° C. for 3 hours, with the addition of triethylamine to aid dissolution. A poly(ether ester urethane) urea elastomer (PEEUU) may be made by reacting polycaprolactone-b-polyethylene glycol-b-polycaprolactone triblock copolymers with 1,4-diisocyanatobutane and putrescine. In a preferred embodiment, PEEUU is obtained by a two-step reaction using a 2:1:1 reactant stoichiometry of 1,4-diisocyanatobutane:triblock copolymer:putrescine. In the first polymerization step, a 15 wt % solution of 1,4-diisocyanatobutane in DMSO is stirred continuously with a 25 wt % solution of triblock compolymer diol in DMSO. In the second step, stannous octoate is added and the mixture is allowed to react at 75° C. for 3 hours. The reaction mixture is then cooled to room temperature and allowed to continue for 18 h. The PEEUU polymer solution is then precipitated with distilled water and the wet polymer is immersed in isopropanol for 3 days to remove unreacted monomer and dried under vacuum.

In another aspects, the valve construct 100 is formed from a sheet of a poly(ester carbonate urethane)urea (PECUU) or poly(carbonate)urethane urea (PCUU) material. PECUU and PCUU are described, for example, in Hong et al. (Tailoring the degradation kinetics of poly(ester carbonate urethane)urea thermoplastic elastomers for tissue engineering scaffolds Biomaterials, doi:10.1016/j.biomaterials.2010.02.005). PECUU is synthesized, for example using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75, and 0/100 (yielding a PCUU)) are completely dissolved in DMSO in a 3-neck flask with argon protection and then BDI is added to the solution, following 4 drops of Sn(Oct)2. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then, the flask is then placed in an oil bath and kept at 70° C. overnight. The polymer is precipitated in an excess volume of cool deionized water and then dried in a vacuum at 60° C. for 3 days. The polyurethane ureas synthesized from the different PCL/PHC molar ratios defined above are referred to as PEUU, PECUU 75/25, PECUU 50/50, PECUU 25/75, and PCUU, respectively. In practice, the yields of all final products using this method is approximately 95%.

Diamines and diols are useful building blocks for preparing the (co)polymer compositions described herein. Diamines, as described above, have the structure $H_2N$—R—$NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as poly-caprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

In additional aspects, the polymer composition comprises polyethylene terephthalate (PET, e.g., DACRON). Of note, PET is less biodegradable than the copolymers described above, and is stiffer. PET scaffolds structures are made essentially in the manner described herein for PEUU and other polymer compositions described herein. Polymer concentrations and infusion rates may be altered to accommodate the different qualities of the PET composition, for example and without limitation, for PET, 20% w/v in HFIP at 12 mL/h infusion rate, as used in the examples below.

In other examples, the polymer composition comprises a tyrosine polyarylate (TPA). As with PET, TPA is less biodegradable than the polyurethane copolymers described above, and is also stiffer. TPA scaffolds structures are made essentially in the manned described herein for PEUU and other polymer compositions. Polymer concentrations and infusion rates may be altered to accommodate the different qualities of the TPA composition, for example and without limitation, for TPA, 12% w/v in HFIP at 20 mL/h infusion rate. Tyrosine polyarylates are commonly prepared from an aliphatic acid and a tyrosine-derived diphenol. Non-limiting examples of useful aliphatic acids include: succinic acid, adipic acid, sebacic acid, and dicarboxylic acid chlorides or anhydrides. Non-limiting examples of tyrosine-derived diphenols include desaminotyrosyl-tyrosine alkyl esters, where the alkyl is, for example, one of ethyl, hexyl, and octyl (DTE). As an example, Poly(DTE-co-27.5 DT succinate) is used. TPAs and methods of making TPAs are described, for example, in U.S. Pat. No. 5,216,115 and U.S. Patent Application Publication No. 2011/0082545, each of which is incorporated herein by reference for its technical disclosure. Additional references disclosing TPA compositions and methods of making and using those compositions include: Fiordeliso, J, et al., *Design, synthesis, and preliminary characterization of tyrosine-containing polyarylates: new biomaterials for medical applications*, J Biomater Sci Polym Ed., 1994; 5(6):497-510; Huang, X, et al., *A library of L-tyrosine-derived biodegradable polyarylates for potential biomaterial applications, part I: synthesis, characterization and accelerated hydrolytic degradation*, J Biomater Sci Polym Ed., 2009; 20(7-8):935-55; and Bourke, S L, et al., *Polymers derived from the amino acid L-tyrosine: polycarbonates, polyarylates and copolymers with poly(ethylene glycol)*, Adv Drug Deliv Rev. 2003 Apr. 25; 55(4):447-66.

The monomer feed ratio and hence the monomer residue composition of any copolymer composition as described herein can be varied so long as the resultant copolymer can be used to manufacture a valve construct as described herein. Variations in the monomer residue composition of copolymer compositions described herein can be readily accomplished and evaluated by one of ordinary skill in the art for usefulness in a heart valve construct.

In one aspect, the valve construct, or sheet used to prepare the valve construct is "wet electrodeposited" meaning a liquid, such as water, saline, PBS, balanced salt solution, or serum-free cell culture medium, is deposited as the polymer is electrodeposited. One method would be to spray the liquid onto a rotating mandrel at the same time the polymer is deposited. In one aspect, the liquid is electrosprayed onto the matrix in substantially the same manner as the polymer is electrospun, the only difference being the deposited liquid is less viscous than the polymer, and the potential difference is such that droplets, rather than fibers, are deposited. As can be recognized by those of ordinary skill in the relevant arts, there are a multitude of salt solutions, buffered salt solutions, media, media supplements, active agents, such as antibiotics, growth factors, and cytokine, biopolymers and ECM-derived material, such as a gel (see, e.g., U.S. Pat. No. 8,361,503, deposited, e.g., as a neutralized pre-gel) that may be electrosprayed onto, or concurrently with the polymer component of the device. Useful media include, without limitation: DMEM, MEM, RPMI 1640, F10, OptiMEM, serum-free media, EMEM, EBM-2, F12, IMDM, and Media 199 (available, e.g., from Invitrogen). Salt solutions include, without limitation: saline, normal saline (approximately 0.9% (w/v)), Dulbecco's phosphate-buffered salines, Hanks' balanced salt solutions, phosphate buffered salined, or Earle's balanced salt solutions. Media supplements include, without limitation: HEPES, Calcium chloride, or sodium bicarbonate. Antibiotics include, without limitation: actinomycin D, ampicillin, carbenicillin, cefotaxime, fosmidomycin, gentamycin, kanmycin, neomycin, penicillin streptomycin, polymyxin B, and streptomycin. Mixtures of more than one media, supplement, or antibiotic can also be used.

In certain aspects, the valve construct 100, and/or sheet 112 used to prepare the valve construct 100 comprises one or more therapeutic agents. For example, at least one therapeutic agent is added to the composition described herein before it is implanted in the patient or otherwise administered to the patient. Generally, the therapeutic agents include any substance that can be coated on, embedded into, absorbed into, adsorbed to, or otherwise attached to or incorporated onto or into the composition described herein or incorporated into a drug product that would provide a therapeutic benefit to a patient. Non-limiting examples of such therapeutic agents include: growth factors, chemoattractants, cytokines, antimicrobial agents, emollients, retinoids, and topical steroids. Each therapeutic agent may be used alone or in combination with other therapeutic agents. For example and without limitation, a composition comprising neurotrophic agents or cells that express neurotrophic agents may be applied to a wound that is near a critical region of the central nervous system, such as the spine.

In certain aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazuril, acyclovir, trifluorouridine, foscarnet, penicillin, gentamicin, ganciclovir, itraconazole, miconazole, Zn-pyrithione, and silver salts such as chloride, bromide, iodide, and periodate.

In certain aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

In certain aspects, cells are added to the material. Non-limiting examples of useful cells include: stem cells, progenitor cells, and differentiated cells; recombinant cells; muscle cells and precursors thereof; nerve cells and precursors thereof; mesenchymal progenitor or stem cells; bone cells or precursors thereof, such as osteoprogenitor cells.

Any useful cytokine, chemoattractant, drug, or cells can be mixed into, mixed with, co-applied, or otherwise combined with any material as described herein. For example and without limitation, useful components include growth factors, interferons, interleukins, chemokines, monokines, hormones, angiogenic factors, drugs, and antibiotics. Cells can be mixed into the material or can be included on or within a sheet, tube, or other device, such as a biological scaffold, combined with the decellularized colonic extracellular matrix material. In either case, when the substrate is seeded with cells, the cells can be grown and/or adapted to the niche created by incubation in a suitable medium in a bioreactor or incubator for a suitable time period to optimally/favorably prepare the composition for implantation in a patient. The substrate can be seeded with cells to facilitate in-growth, differentiation, and/or adaptation of the cells. For example and without limitation, the cells can be autologous or allogeneic with respect to the patient to receive the composition/device comprising the gel. The cells can be stem cells or other progenitor cells, or differentiated cells. In one example, a layer of dermis obtained from the patient is seeded on a mold, for use in repairing damaged skin and/or underlying tissue.

As used herein, the terms "therapeutic agent" and "therapeutic agents" refer to any composition(s), such as drug(s) or active agent(s) having a preventative or therapeutic effect, including and without limitation, antibiotics, peptides, hormones, organic molecules, vitamins, supplements, factors, proteins, and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

In some aspects, the valve construct 100 is formed from a porous deposited biodegradable, elastomeric polymer. As used herein, the term "porosity" refers to a ratio between a volume of all the pores within the polymer composition and a volume of the whole polymer composition. For instance, a polymer composition with a porosity of 85% would have 85% of its volume containing pores and 15% of its volume containing the polymer. In certain non-limiting embodiments, the porosity of the structure is at least 60%, 65%, 70%, 75%, 80%, 85%, or 90%, or increments therebetween. In another non-limiting example, an average pore size of the structure is between 0.1 and 300 microns, preferably between 0.1 and 100 microns, and more preferably between 1-25 microns, including increments therebetween. For example and without limitation, a structure that acts as a barrier to bacteria and other pathogens may have an average pore size of less than 0.5 microns or less than 0.2 microns.

In some examples, the polymer composition of the valve construct 100 further comprises, for example and without limitation, a biomacromolecular component derived from ECM. In one example, the polymer composition comprises the biomacromolecule collagen so that collagenase, which is present in situ, can degrade the collagen. As an example, the polymer composition may comprise one or both of a collagen and an elastin. Collagen is a common ECM component, and typically is degraded in vivo at a rate faster than many synthetic bioerodable polymers. Therefore, manipulation of collagen content in the polymer composition may be used as a method of modifying bioerosion rates in vivo. Collagen may be present in the polymer composition in any useful range, including, without limitation, from about 2% wt. to about 95% wt., preferably in a range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting example, collagen and elastin are present in approximately equal amounts in the polymer composition. In another embodiment, the sum of the collagen and elastin content in the polymer composition is in any useful range, including, without limitation, from about 2% wt. to about 95% wt., and preferably in the range of from about 25% wt. to about 75% wt., inclusive of all ranges and points therebetween, including from about 40% wt. to about 75% wt., including about 75% wt. and about 42.3% wt.

In a further aspect, a kit is provided comprising a template or cutting guide (such as the template 10 shown in FIGS. 1-4B) and a sheet (such as sheet 112) of a porous deposited biodegradable, elastomeric polymer or ECM derived material described herein. Portions of the kit can be packaged in a container. In some instances, the container can be formed from a portion of the porous material or sheet. The container can be suitable for storage and transfer of the contents of the kit in commercial distribution routes of the kit.

Alternative Template Configurations

Figure 6:
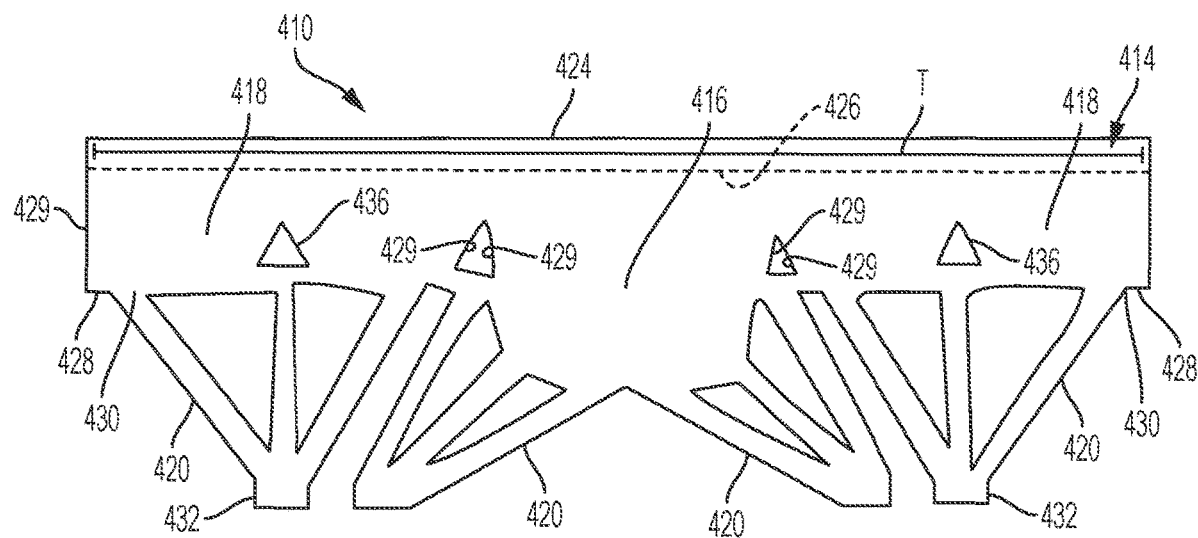
FIG. 6 is a top view of another embodiment of a template for a heart valve construct for replacement or repair of a mitral valve according to an aspect of the disclosure.

With reference to FIG. 6, another exemplary template 410 is illustrated. The template 410 is configured to produce a valve construct for a mitral valve. The template 410 includes an anterior leaflet portion 416 positioned between posterior leaflet portions 418. The leaflet portions 416, 418 each comprise a proximal edge 426, a distal edge 428, and side edges 429 extending between the proximal edge 426 and the distal edge 428. The template 410 further comprises a plurality of substantially straight elongated chordae portions 420 each having a proximal end 430 connected to the distal edge 428 of one of the leaflet portions 416, 418 and a distal end 432 extending therefrom. The template 410 is sized such that a total width of the leaflet portions 416, 418 (shown by line T in FIG. 6) of the template 410 is substantially equal to a circumference of a native annulus of a heart valve. In some examples, a sewing ring portion 414 is sized to be connected to the valve annulus. For example, a proximal free edge 424 of the sewing ring 414 can be sutured to a circumference of the valve annulus.

Compared to the exemplary templates in FIGS. 1-4B, the template of FIG. 6 includes a narrower and shorter anterior leaflet portion 416. To compensate for the narrowed anterior leaflet portion 416, in the example template 410 of FIG. 6, a width of the posterior leaflet portion 418 has been increased. The template 410 also includes one or more slits 436 on the posterior leaflet portions 418, which are not present in previous examples. Features of the template 410 have also been designed to be more angular, including longer straight segments, to make it easier to cut out the valve construct using the template 410.

Figure 7:
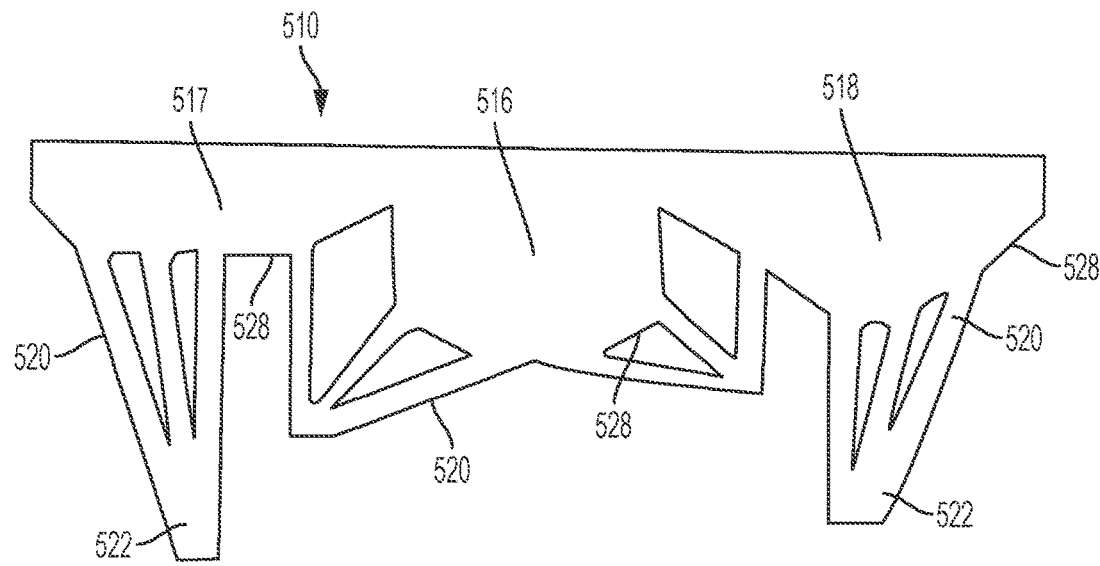
FIG. 7 is a top view of another embodiment of a template for a heart valve construct for replacement or repair of a tricuspid valve according to an aspect of the disclosure.

A template 510 for a tricuspid valve including features of the template 410 is shown in FIG. 7. As shown in FIG. 7, the template 510 includes a central anterior leaflet portion 516, positioned between a posterior leaflet portion 518 and a septal leaflet portion 517. The template 510 also includes chordae portions 520 extending from distal ends 528 of the leaflet portions 516, 517, 518. Specifically, groups of three chordae portions 520 extend from the posterior leaflet portion 518 and the septal leaflet portion 517 to respective head portions 522. In addition, groups of two chordae portions 520 extend from opposing sides of the anterior leaflet portion 516 and connect to a single chordae portion 520 extending from the posterior leaflet portion 518 and the septal leaflet portion 517, respectively.

Figure 8A:
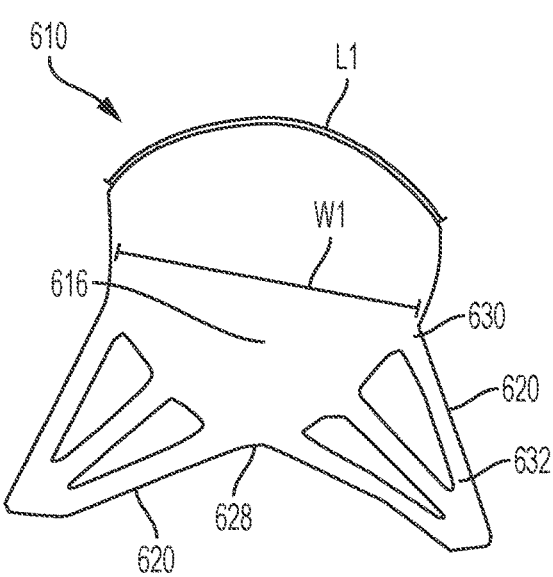
FIGS. 8A and 8B are top views of portions of another embodiment of a template for a heart valve construct for replacement or repair of a mitral valve including separate leaflet portions according to an aspect of the disclosure.
Figure 8B:
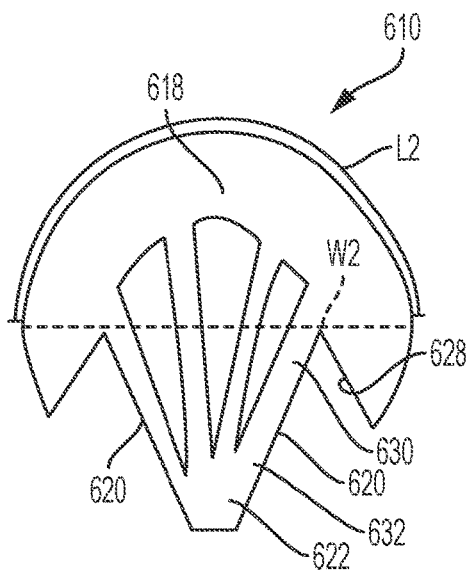

With reference to FIGS. 8A and 8B, another example of a template 610 for a mitral valve is illustrated, including an anterior leaflet portion 616 and a separate posterior leaflet portion 618. The anterior leaflet portion 616 as a proximal end length L1 and a width W1. The posterior leaflet portion 618 has a proximal end length L2 and a width W2. A total length (e.g., L1+L2) and a total width (e.g., W1+W2) of the leaflet portions 616, 618 is sized to correspond to a circumference of a native valve annulus of a heart valve. As in previous examples, the template 610 also includes a plurality of substantially straight elongated chordae portions 620 each having a proximal end 630 connected to the distal edge 628 of one of the respective leaflet portions 616, 618 and a distal end 632 opposite the proximal end 630. The template 610 also includes one or more papillary muscle head portions 622 formed at a commissure between distal ends 632 of at least two of the plurality of chordae portions 620.

Figure 9A:
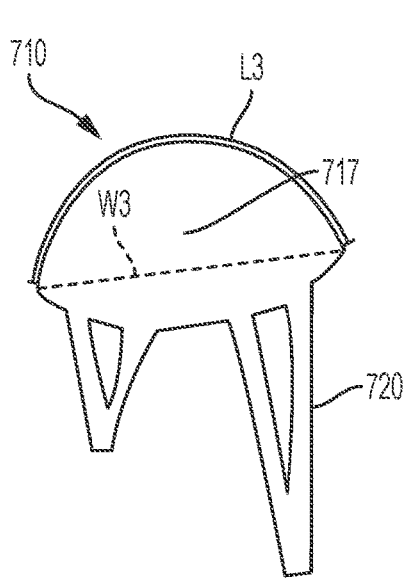
FIGS. 9A-9C are top views of portions of another embodiment of a template for a heart valve construct for replacement or repair of a tricuspid valve including separate leaflet portions according to an aspect of the disclosure.
Figure 9B:
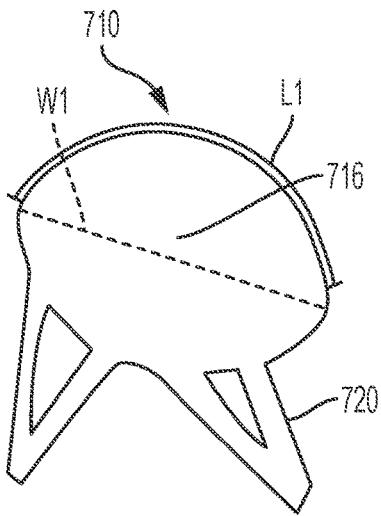
Figure 9C:
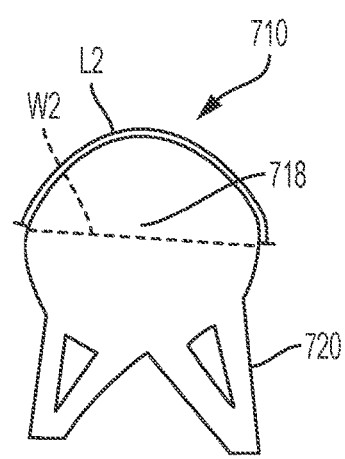

With reference to FIGS. 9A-9C, an example of a template 710 including a separate anterior leaflet portion 716, septal leaflet portion 717, and posterior leaflet portion 718 is illustrated. The leaflet portions 716, 717, 718 have a proximal length L1, L2, L3, and width W1, W2, W3 sized to correspond to a circumference of a native annulus of a heart valve. For example, a total proximal length (e.g., L1+L2+L3) and/or total width (e.g., W1+W2+W3) of the template 710 can be substantially equal to the circumference of a native annulus of a heart valve. As shown in FIGS. 9A-9C, the template 710 also includes four elongated chordae portions 720 extending from each of the leaflet portions 716, 717, 718. The elongated chordae portions 720 are divided into groups of two chordae portions 720 extending from opposing sides of each leaflet portion 716, 717, 718. As in previous examples, chordae portions 720 have a width of about 2 mm and a length of about 16 mm to about 22 mm.

Method of Forming a Valve Construct

Figure 10:
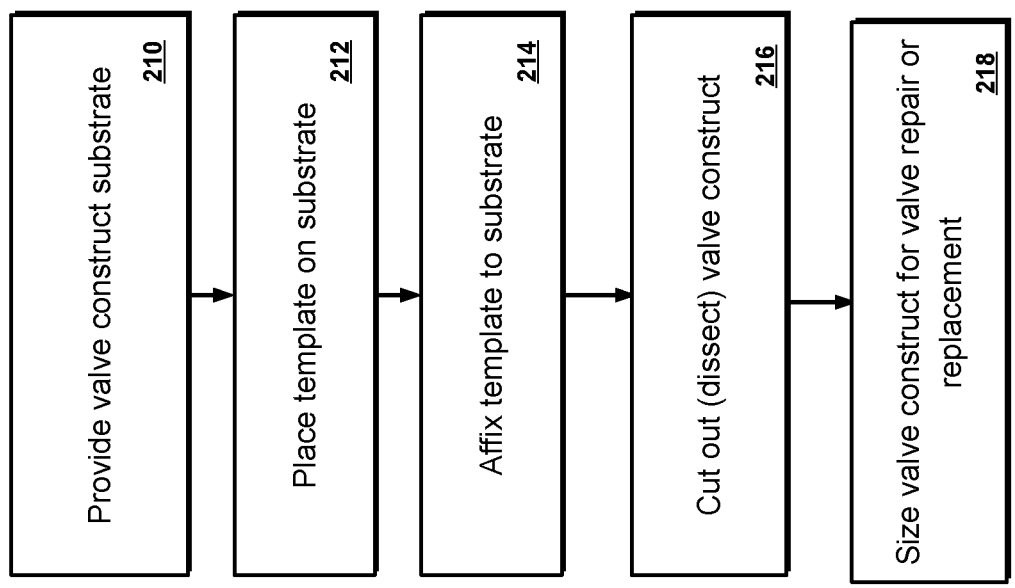
FIG. 10 is a flow chart of a method for forming a valve construct for replacement of a mitral or tricuspid valve using a template according to an aspect of the disclosure.

As shown in FIG. 10, steps for forming a valve construct from a natural or synthetic substrate as directed by a cutting guide are illustrated. The cutting guide can be one or more of the above-described templates. As used herein, a template refers to a structure or device defining an outline of a shape. A template is used to produce the shape by, for example, tracing or cutting along an edge of the template. In some examples, the template is a "positive template" that covers material in, for example, a valve construct shape to be retained and, therefore, having edges or borders that define the shape to be produced, and exposed material is cut away (dissected) from the material to be retained, e.g., as a valve construct. The positive template is, therefore, shaped, at least in part, as a valve construct. Exemplary positive templates in the shape of a valve construct are shown in FIGS. 1-4B and 6-9C. In other examples, a template is a "negative template" or stencil that covers material to be removed or dissected from the final product, e.g., valve construct and, therefore, having edges or borders that defines the shape to be produced, and exposed material is retained for use as a valve construct. In order to produce the valve construct shape, a user traces or cuts around the edges or borders of the negative template to produce the desired shape. In most instances, a positive template, that is, a template covering and protecting material to be retained for use as a valve construct, is preferred and is easier to use and implement.

As shown in box 210, the method includes providing a suitable substrate for the valve construct. As described herein, the substrate can be natural material such as pericardium. In a general sense, pericardium is a biodegradable, biomacromolecular component, including an extracellular matrix (ECM)-derived material, for example, decellularized tissue. The substrate can also be a synthetic material, such as a porous, fibrous polymer substrate. The polymer substrate can be formed by an electrospinning process.

Steps are then performed to cut and/or form the valve construct from the provided substrate. For example, as shown at box 212, a template is placed on the substrate. Optionally, as shown at box 214, the template may be temporarily affixed to the substrate with, for example, an adhesive. As shown at box 216, a surgeon then dissects portions of the substrate away from the template using, for example, a scalpel to produce the valve construct. As used herein, dissecting the substrate can include pressing the scalpel blade into the substrate to form a cut or incision. Dissecting the substrate can also include drawing or pulling the blade through the substrate to lengthen the cut or incision. Dissecting can also include using a scalpel to pull portions of the substrate away from the template to widen the cut or incision or to release the desired valve construct shape from other portions of the provided substrate. After the desired shape is released from other portions of the provided substrate to form the valve construct, the template can be removed and the prepared valve construct may be prepared for implantation. When performing a partial valve replacement or valve repair, as shown at box 218, the surgeon can size the valve construct for a particular valve repair or replacement being performed. For example, the surgeon can cut portions from the formed valve construct for use in the partial repair.

In another aspect, the cutting guide is a stamp, die, or cutter (e.g., a cookie cutter) having a sharpened edge or ridge in the shape of the valve construct. The stamp, die, or cutter is configured to be pressed into the substrate to cut the shape from the substrate. For example, a stamp or die includes a body having a flat surface with a raised ridge extending therefrom. The ridge forms an enclosed outline of the valve construct shape. A peak of the ridge may be sharpened so that it can easily impinge and cut the substrate to form the valve construct shape.

In another aspect, the cutting guide comprises a series of digital and/or computer instructions or routines which can be read by a computerized device, such as an automatic cutting machine or three-dimensional printer, and which cause the computerized device to perform a cutting and/or shape-forming action. For a cutting machine, the computer instructions may cause a cutting element of an automatic cutting machine to move along the surface of the substrate in a predetermined pattern. As the cutting element moves along the surface of the substrate, a blade may automatically extend from the cutting element and through the substrate at a predetermined position on the substrate surface. Continued movement of the cutting element along the surface of the substrate in the predetermined pattern cuts the shape from the substrate to form the valve construct. In other examples, the blade may be replaced with an energy beam (e.g., a laser cutter), plasma beam, cauterizing element, or similar structure depending on the material characteristics of the substrate being cut.

For a three-dimensional printer, the computer instructions may cause a print-head of the printer to move along the substrate surface in a predetermined pattern. The print-head is configured to deposit a thin layer of material (e.g., a flowable and curable polymer material) to the substrate in a shape of a bottom-most layer of the valve construct shape. In some examples, a curing element of the print-head cures the flowable polymer material to a desired position on the substrate immediately following deposition. After the first or bottom-most layer is deposited, the print-head may move along the substrate a second time in the predetermined pattern to deposit a second layer of material on the first layer. Multiple layers may be deposited on top of one another in this manner to produce a valve construct of an appropriate thickness. Depending upon the resolution and sensitivity of the three-dimensional printer being used, the various deposited layers may include pores, openings, filaments, or other structural features to impart certain functional characteristics for the formed valve construct.

Method of Implanting a Valve Construct

Figure 11:
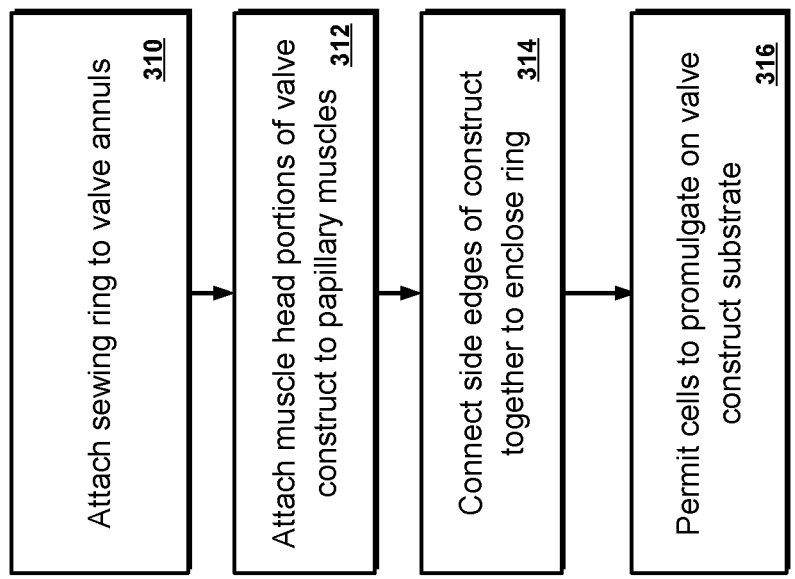
FIG. 11 is a flow chart of a method for implanting a valve construct according to an aspect of the disclosure.
Figure 12A:
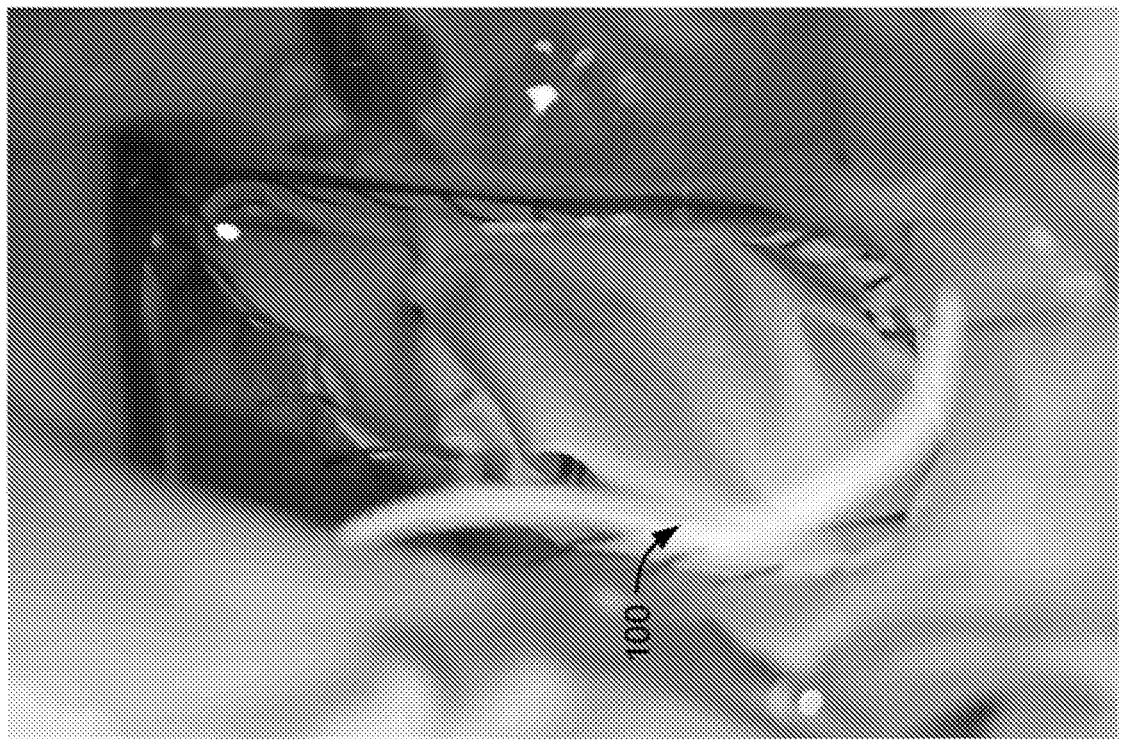
FIG. 12A is a photograph of a coaptation experiment performed ex vivo with a polyurethane valve construct in the mitral position before PBS infusion.
Figure 12B:
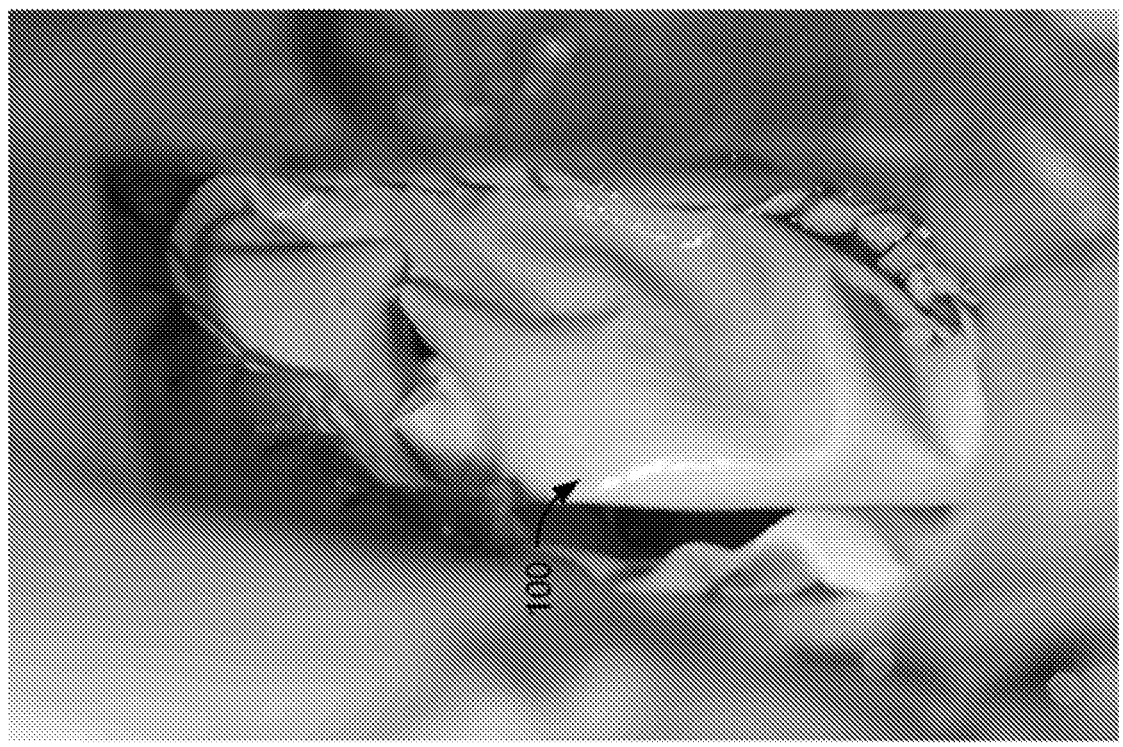
FIG. 12B is a photograph of the valve construct of FIG. 12A after PBS infusion and coaptation.
Figures 13A, 13B:
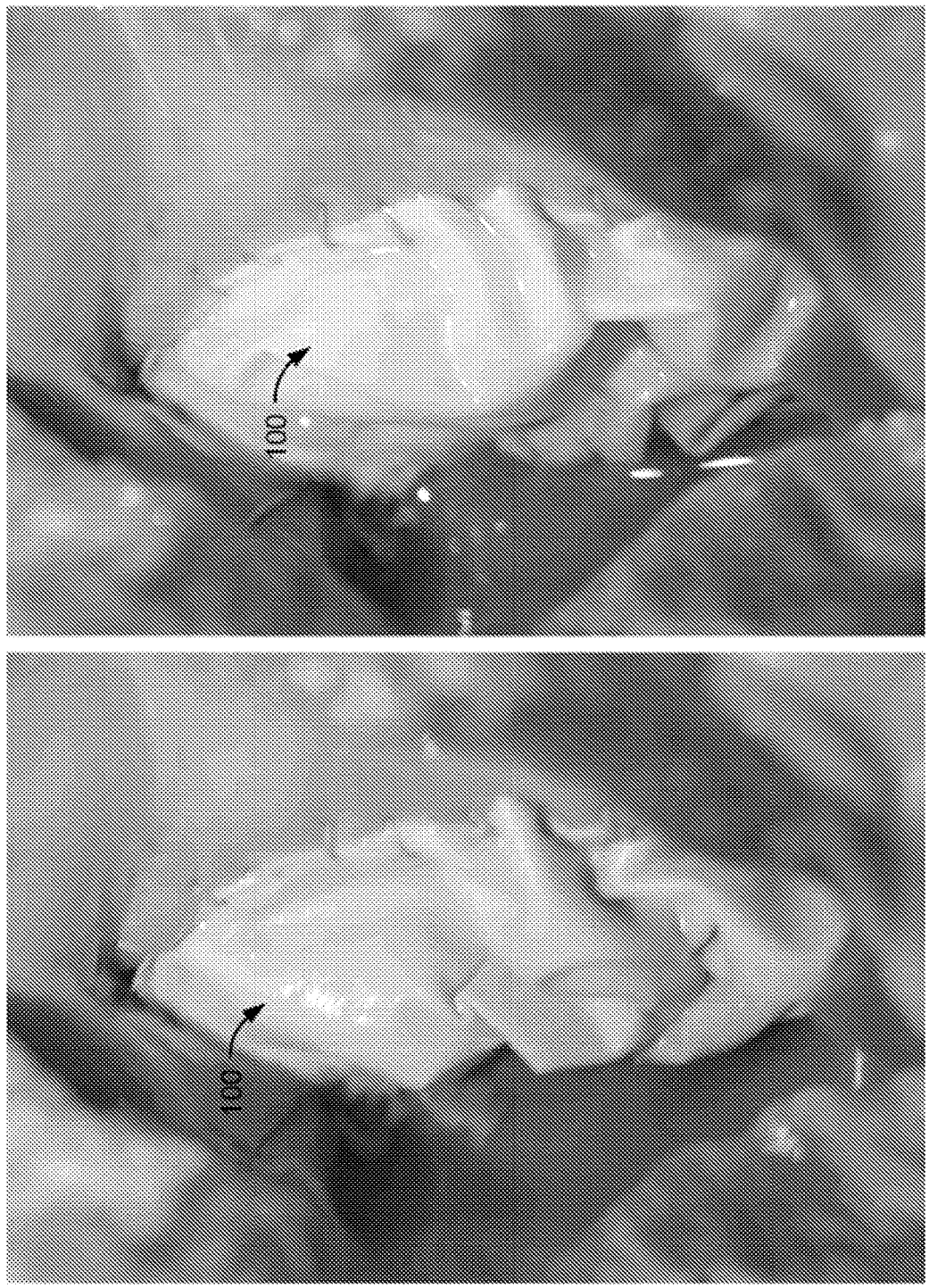
FIG. 13A is a photograph of a coaptation experiment performed ex vivo with a polyurethane single template valve construct in the tricuspid position before PBS infusion.
FIG. 13B is a photograph of the valve construct of FIG. 13A after PBS infusion and coaptation.
Figure 14B:
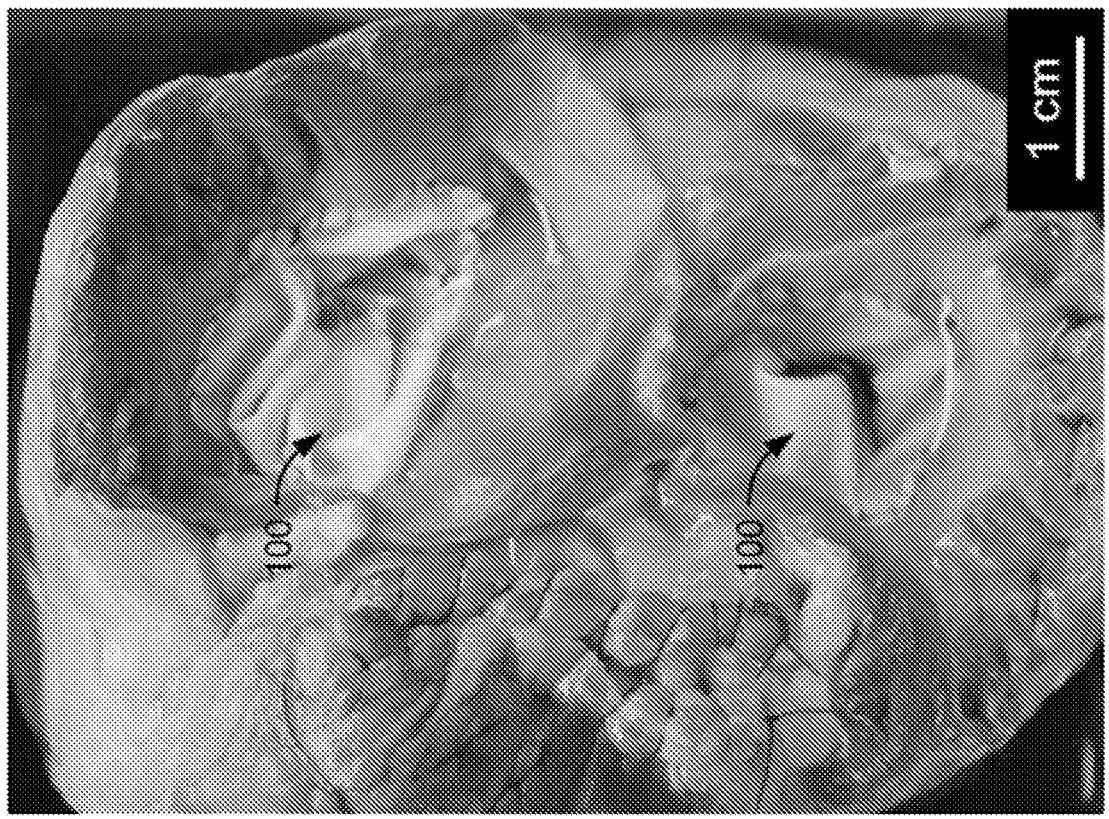
FIG. 14B is a photograph of the valve construct of FIG. 14A after PBS infusion and coaptation.
Figure 14A:
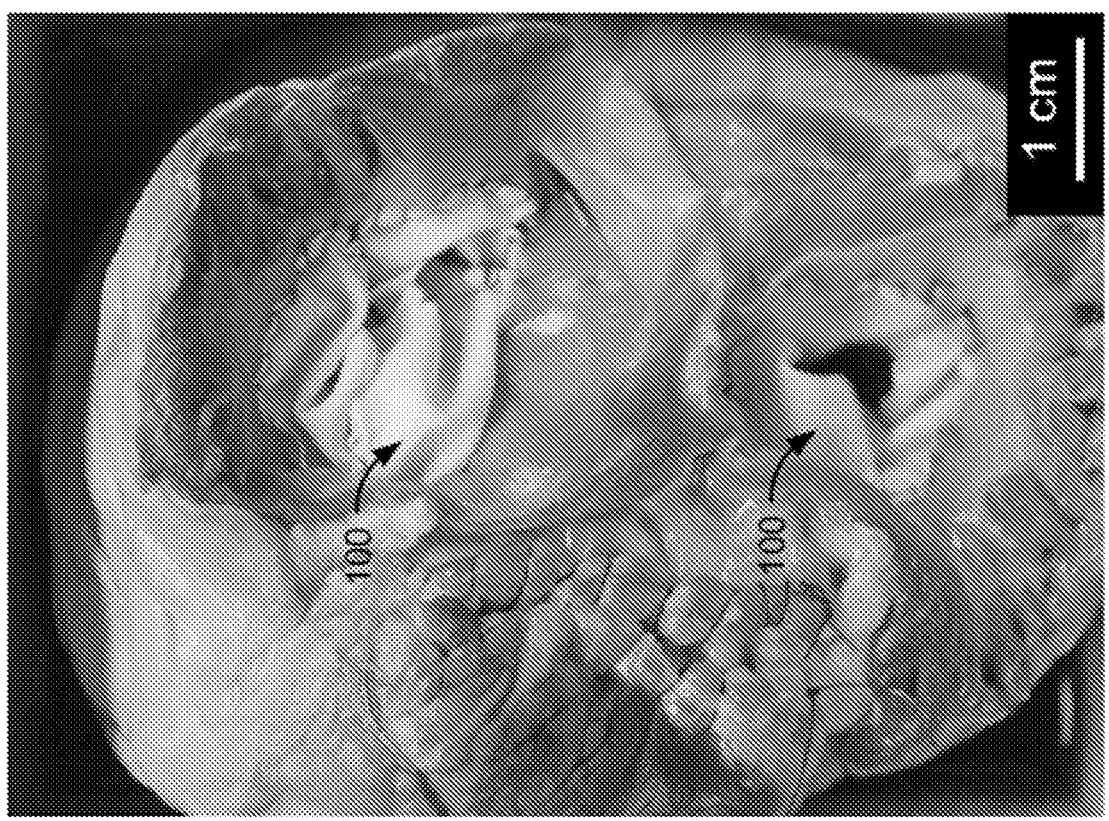
FIG. 14A is a photograph of a coaptation experiment ex vivo with a polyurethane leaflet template valve construct in both the mitral and tricuspid positions before PBS infusion.

As shown in FIG. 11, steps for implanting a valve construct in a valve annulus of a patient are illustrated. As shown at box 310, the proximal sewing ring of the valve construct is sutured around the circumference of the valve annulus. For example, a running suture technique with polypropylene sutures may be used for connecting the valve construct to the valve annulus. As shown at box 312, the capillary muscle head portions at the commissure between adjacent chordae tendineae are then sewn to the papillary muscles in the ventricle. As shown at box 314, the side edges of the sewing ring portion of the valve construct can also be sewn together to form an enclosed ring extending around the circumference of the valve annulus. As shown at box 316, once the valve construct is in place in the mitral or tricuspid position, cells are permitted to promulgate to the valve construct as the construct degrades. As such, over time, the material of the valve construct is replaced by regenerated tissue.

EXAMPLES

Example 1: Determining Valve Construct Dimensions and Geometry

While the above-described sizes and dimensions are provided as exemplary dimensions for a template 10, 410, 510, 610, 710 and valve construct 100 for an average sized individual, as will be appreciated by one of ordinary skill in the art, such dimensions may be optimized based on available or later acquired anatomical data for particular patient populations.

One proposed routine for obtaining such dimensional data involves studying in vitro three-dimensional images of porcine heart valves acquired with micro-computed tomography (micro-CT). Such analysis could allow for a determination of detailed and accurate geometry of the mitral and tricuspid valves based on subject size. Sampling a variety of porcine heart sizes could show how native physiology changes the dimensions on the leaflets, length of the chordae, number of chordae, chordae branching, and chordae attachment position on the leaflets as the body size changes. In some instances, micro-CT 3D images obtained of the porcine heart valve can be converted to a finite element (FE) model and used to assess leaflet stresses and function for different complex valve geometries. In a similar manner, an algorithm can be developed to determine the subject-specific anatomy and dimensions based on the size of the patient. Such a computation model would then be applied to the optimized valve parameters (e.g., leaflet width height, chordae length, etc.) to the template valve for a particular patient.

Example 2: Proof of Concept Experimental Protocol

Proof-of-concept mitral and tricuspid valve templates of the shape and size described herein were cut from Teflon sheets. The Teflon templates were placed on an electrospun polyurethane sheet or substrate. A surgeon cut out valve constructs from the polyurethane sheet using a scalpel by following the shape of the template. A fresh porcine heart was provided for implantation. After dissecting the mitral and tricuspid valves from the porcine heart, the surgeon implanted the polyurethane valve construct using a polypropylene 0 running suture for the annulus while also suturing the template chordae to the papillary muscles in the ventricle.

Template valve coaptation was tested ex vivo by filling the ventricle with phosphate-buffer solution (PBS). Briefly, a silicone tube attached to a syringe filled with PBS was inserted between the valve construct leaflets and into the ventricle. PBS was infused manually into the ventricle causing the leaflets to coapt as seen in FIGS. 9A-11B (before and are filling). Single template mitral and tricuspid valves are shown in FIGS. 9A-10B. FIGS. 11A and 11B show a porcine heart in which both the mitral and tricuspid valves have been replaced with individual leaflet template valves.

Future experiments may monitor atrio-ventricular pressure as the ventricle is filled with PBS by using a Mikro-Cath™ pressure catheter (Millar Inc., Houston, Tex.) in the apex of the heart to test coaptation at physiologically relevant pressures. Suturing the aortic arch and pulmonary trunk closed at the aortic and pulmonary valves will allow the pressure to be accurately measured in the left and right ventricles, respectively. Pressure signals will be monitored and recorded with a custom LabView script while a Rebel T3 camera (Canon Inc., Melville, N.Y.) will record synchronized digital images.

While several examples and embodiments of the template, valve construct, and treatment methods are shown in the accompanying figures and described hereinabove in detail, other examples and embodiments will be apparent to, and readily made by, those skilled in the art without departing from the scope and spirit of the invention. For example, it is to be understood that this disclosure contemplates that, to the extent possible, one or more features of any embodiment can be combined with one or more features of any other embodiment. Accordingly, the foregoing description is intended to be illustrative rather than restrictive.

Preferred and non-limiting aspects or embodiments of the present invention will now be described in the following numbered clauses:

Clause 1: A template for a valve construct for replacement of at least one of a mitral valve and a tricuspid valve, the template comprising: at least an anterior leaflet portion and at least a posterior leaflet portion, each leaflet portion comprising a proximal edge, a distal edge, and side edges extending between the proximal edge and the distal edge; a plurality of substantially straight elongated chordae portions each having a proximal end connected to the distal edge of one of the at least two leaflet portions and a distal end extending therefrom; and one or more papillary muscle head portions formed at a commissure between distal ends of at least two of the plurality of chordae portions, wherein a total width of the leaflet portions of the template is substantially equal to a circumference of a native annulus of a heart valve.

Clause 2: The template of clause 1, wherein the anterior leaflet portion is separate from the posterior leaflet portion.

Clause 3: The template of clause 1, further comprising a sewing ring portion extending along a proximal longitudinal free edge of the template, wherein a distal edge of the sewing ring portion is co-extensive with the proximal edges of the at least one anterior leaflet portion and the at least a posterior leaflet portion.

Clause 4: The template of any of clauses 1 to 3, wherein the distal edges of the anterior and posterior leaflet portions comprise a plurality of substantially straight segments.

Clause 5: The template of clause any of clauses 1 to 4, wherein the plurality of chordae portions each comprise substantially straight segments having a width of about 2 mm.

Clause 6: The template of any of clauses 1 to 5, wherein the total width of the at least one anterior leaflet portion and the at least a posterior leaflet portion is about 7 cm to 11 cm.

Clause 7: The template of any of clauses 1 to 6, wherein a height of one of the anterior leaflet portion is three times greater than a height of the posterior leaflet portion.

Clause 8: The template of any of clauses 1 to 7, wherein a first group of chordae portions extends from a first portion of the distal edge of the at least one anterior portion to a first commissure and a second group of chordae portions extends from a second portion of the distal edge of the anterior portion to a second commissure.

Clause 9: The template of clause 8, wherein the anterior leaflet portion is between first and second posterior leaflet portions.

Clause 10: The template of any of clauses 1 to 9, wherein, for a tricuspid valve template, the template further comprises a septal leaflet portion, and wherein the septal and posterior leaflet portions have a height of 3A and the anterior leaflet portion has a height of 4A, where A is defined as ⅙ of a diameter of a valve annulus of the tricuspid valve.

Clause 11: The template of any of clauses 1 to 10, wherein the plurality of chordae portions have a longitudinal length of about 16 mm to about 22 mm.

Clause 12: The template of any of clauses 1 to 11, wherein for a tricuspid valve construct, chordae portions near an anteroposterior commissure side of the template are longer than chordae portions on an opposite side thereof.

Clause 13: The template of any of clauses 1 to 12, further comprising a plurality of transverse chordae portions extending between the anterior leaflet portion and the posterior leaflet portion.

Clause 14: The template of any of clauses 1 to 13, wherein the template is formed from a single substantially flat sheet.

Clause 15: The template of any of clauses 1 to 14, wherein the anterior leaflet portion is formed from a first substantially flat sheet and the posterior leaflet portion is formed from a second substantially flat sheet.

Clause 16: The template of any of clauses 1 to 15, wherein the template is formed from one or more flat sheets of stainless steel stock.

Clause 17: The template of any of clauses 1 to 16, wherein the papillary muscle head portions are formed at a commissure between at least three chordae portions extending from the same leaflet portion.

Clause 18: A kit of parts comprising the template of any of clauses 1 to 17 and a flat sheet formed from a natural or synthetic biocompatible material configured to be formed into a valve construct with the template.

Clause 19: The kit of clause 18, further comprising a scalpel for cutting the flat sheet into the valve construct.

Clause 20: A valve construct formed according to a cutting guide, the valve construct comprising a flat sheet formed from a natural or synthetic biocompatible material, the sheet comprising: at least an anterior leaflet portion and at least a posterior leaflet portion, each leaflet portion comprising a proximal edge, a distal edge, and side edges extending between the proximal edge and the distal edge; a plurality of substantially straight elongated chordae portions each having a proximal end connected to the distal edge of one of the at least two leaflet portions and a distal end extending therefrom; and one or more papillary muscle head portions formed at a commissure between distal ends of at least two of the plurality of chordae portions, wherein a total width of the leaflet portions of the template is substantially equal to a circumference of a native annulus of a heart valve.

Clause 21: The valve construct of clause 20, wherein the anterior leaflet portion is separate from the posterior leaflet portion.

Clause 22: The valve construct of clause 20, further comprising a sewing ring portion extending along a proximal longitudinal free edge of the valve construct, wherein a distal edge of the sewing ring portion is co-extensive with the proximal edges of the at least one anterior leaflet portion and the at least a posterior leaflet portion.

Clause 23: The valve construct of any of clauses 20 to 22, wherein the distal edges of the anterior and posterior leaflet portions comprise a plurality of substantially straight segments.

Clause 24: The valve construct of any of clauses 20 to 23, wherein the plurality of chordae portions each comprise substantially straight segments having a width of about 2 mm.

Clause 25: The valve construct of any of clauses 20 to 24, wherein the total width of the at least one anterior leaflet portion and the at least a posterior leaflet portion is about 7 cm to 11 cm.

Clause 26: The valve construct of any of clauses 20 to 25, wherein the sheet comprises a natural fibrous material configured to promote tissue growth.

Clause 27: The valve construct of any of clauses 20 to 26, wherein the material comprises a material which degrades in vivo.

Clause 28: The valve construct of any of clauses 20 to 27, wherein the material comprises a porous polymer material.

Clause 29: The valve construct of any of clauses 20 to 29, wherein for a tricuspid valve construct, chordae portions near an anteroposterior commissure side of the template are longer than chordae portions on an opposite side thereof.

Clause 30: A method of forming an implantable valve construct, comprising: providing a substantially flat substrate of a natural or synthetic biocompatible material; and cutting a shape from the substantially flat sheet as directed by a cutting guide to form the valve construct, wherein the shape comprises: at least an anterior leaflet portion and at least a posterior leaflet portion, each leaflet portion comprising a proximal edge, a distal edge, and side edges extending between the proximal edge and the distal edge; a plurality of substantially straight elongated chordae portions each having a proximal end connected to the distal edge of one of the at least two leaflet portions and a distal end extending therefrom; and one or more papillary muscle head portions formed at a commissure between distal ends of at least two of the plurality of chordae portions, wherein a total width of the leaflet portions of the template is substantially equal to a circumference of a native annulus of a heart valve.

Clause 31: The method of clause 30, wherein the cutting guide comprises one or more of a positive template, a negative template, a stencil, a stamp, and a cutting protocol for an automatic cutting machine, and a printing protocol for a three-dimensional printer.

Clause 32: The method of clause 30, wherein the cutting guide comprises a template, and wherein cutting the shape from the substantially flat sheet comprises: placing the template for the valve construct on the substrate; and dissecting the substrate about the template to form the valve construct.

Clause 33: The method of clause 30, wherein the cutting guide comprises a cutting protocol for an automatic cutting machine, and wherein cutting the shape from the substantially flat sheet comprises: positioning the cutting machine to cut one or more curved incisions through the substrate; and operating the cutting machine to cut the shape from the substrate to form the valve construct.

Clause 34: The method of any of clauses 30 to 33, further comprising sizing or sectioning the valve construct so that the valve construct is a suitable size and shape for performing a valve repair procedure.

Clause 35: The method of any of clauses 30 to 34, wherein the anterior leaflet portion of the shape is separate from the posterior leaflet portion of the shape.

Clause 36: The method of any of clauses 30 to 34, wherein the shape further comprises a sewing ring portion extending along a proximal longitudinal free edge thereof, and wherein a distal edge of the sewing ring portion is co-extensive with the proximal edges of the at least one anterior leaflet portion and the at least a posterior leaflet portion.

Clause 37: The method of any of clauses 30 to 37, wherein the distal edges of the anterior and posterior leaflet portions comprise a plurality of substantially straight segments.

Clause 38: The method of any of clauses 30 to 37, wherein the plurality of chordae portions each comprise substantially straight segments having a width of about 2 mm.

Clause 39: The method of any of clauses 30 to 38, wherein the total width of the at least one anterior leaflet portion and the at least a posterior leaflet portion is about 7 cm to 11 cm.

Clause 40: A method for performing a valve repair or valve replacement procedure by implanting a natural or synthetic valve construct to a valve annulus of a patient, comprising: dissecting at least one of a mitral or tricuspid valve of the patient to reveal structures of the valve annulus; attaching a portion of the valve construct to the valve annulus by suturing a free proximal edge of the valve construct to the valve annulus; attaching muscle head portions of the valve construct to papillary muscles of a ventricle of the patient; and connecting side edges of the construct together to form an enclosed ring, wherein the valve construct comprises: at least an anterior leaflet portion and at least a posterior leaflet portion, each leaflet portion comprising a proximal edge, a distal edge, and side edges extending between the proximal edge and the distal edge; a plurality of substantially straight elongated chordae portions each having a proximal end connected to the distal edge of one of the at least two leaflet portions and a distal end extending therefrom; and one or more of the papillary muscle head portions formed at a commissure between distal ends of at least two of the plurality of chordae portions, and wherein a total width of the leaflet portions of the valve construct is substantially equal to a circumference of a native annulus of a heart valve.

Clause 41: The method of clause 40, further comprising selecting an appropriately sized valve construct for the procedure to be performed from a kit of pre-fabricated valve constructs sized for different patients.

Clause 42: The method of clause 40 or clause 41, further comprising, prior to attaching the portion of the valve construct to the valve annulus, manually sectioning and sizing the selected pre-fabricated valve construct to customize the valve construct for the valve replacement or repair procedure being performed.

Clause 43: The method of any of clauses 40 to 42, wherein the valve construct further comprises a sewing ring portion extending along the proximal longitudinal free edge of the valve construct, wherein a distal edge of the sewing ring portion is co-extensive with the proximal edges of the at least one anterior leaflet portion and the at least a posterior leaflet portion.

Clause 44: The method of clause 43, wherein attaching a portion of the valve construct to the valve annulus comprises suturing the sewing ring portion of the valve construct to the valve annulus.

Clause 45: A method of forming an implantable valve construct comprising forming a substrate of a natural or synthetic biocompatible material into a predetermined shape to form the valve construct, wherein the predetermined shape comprises: at least an anterior leaflet portion and at least a posterior leaflet portion, each leaflet portion comprising a proximal edge, a distal edge, and side edges extending between the proximal edge and the distal edge; a plurality of substantially straight elongated chordae portions each having a proximal end connected to the distal edge of one of the at least two leaflet portions and a distal end extending therefrom; and one or more papillary muscle head portions formed at a commissure between distal ends of at least two of the plurality of chordae portions, wherein a total width of the leaflet portions of the template is substantially equal to a circumference of a native annulus of a heart valve.

Clause 46: The method of clause 45, wherein forming the substrate into the predetermined shape comprises by one or more of the following processes: electrospinning, double component electrospinning, wet electrospinning, melt spinning, jet spinning, extrusion spinning, gel spinning, thermally induced phase separation processing, gas foaming processing, and particle leaching processing.

Clause 47: The method of clause 45, wherein forming the substrate into the predetermined shape comprises printing the substrate using a three-dimensional printer and a computer-implemented protocol for a three-dimensional printer configured to produce the predetermined shape.

What is claimed is:

1. A template for a valve construct for replacement of at least one of a mitral valve or a tricuspid valve, the template comprising:
    an anterior leaflet portion;
    at least two additional leaflet portions, wherein each of the leaflet portions comprises a proximal edge, a distal edge, and side edges extending between the proximal edge and the distal edge, and wherein the anterior leaflet portion is connected to and positioned between the at least two additional leaflet portions;
    a plurality of substantially straight elongated chordae portions each having a proximal end connected to the distal edge of the anterior leaflet portion or the at least two additional leaflet portions and a distal end extending therefrom; and
    at least one papillary muscle head portion formed at a commissure between (i) distal ends of at least two of the plurality of chordae portions extending from the anterior leaflet portion and (ii) a distal end of a third chordae portion extending from one of the at least two additional leaflet portion,
    wherein the at least one papillary muscle head portion is spaced apart laterally and longitudinally from the anterior leaflet portion, and
    wherein a total width of the proximal edges of the anterior leaflet portion and the at least two additional leaflet portions of the template is substantially equal to a circumference of a native annulus of a heart valve.

2. The template of claim 1, further comprising a sewing ring portion extending along a proximal longitudinal free edge of the template, wherein a distal edge of the sewing ring portion is co-extensive with the proximal edges of the anterior leaflet portion and the at least two additional leaflet portions.

3. The template of claim 1, wherein the distal edges of the anterior leaflet portion and the at least two additional leaflet portions comprise a plurality of straight segments.

4. The template of claim 1, wherein the plurality of chordae portions each comprise straight segments having a width of about 2 mm.

5. The template of claim 1, wherein the total width of the anterior leaflet portion and the at least two additional leaflet portions is about 7 cm to about 11 cm.

6. The template of claim 1, wherein a height of the anterior leaflet portion is three times greater than a height of the at least two additional leaflet portions.

7. The template of claim 1, wherein the template is for a tricuspid valve with the at least two additional leaflet portions comprising (i) a posterior leaflet portion, and (ii) a septal leaflet portion, wherein a first group of chordae portions extends from a first portion of the distal edge of the anterior leaflet portion to a first commissure and a second group of chordae portions extends from a second portion of the distal edge of the anterior leaflet portion to a second commissure.

8. The template of claim 7, wherein the third chordae portion extends from the septal leaflet portion to the first commissure and a fourth chordae portion extends from the posterior leaflet portion to the second commissure.

9. The template of claim 1, wherein, for a tricuspid valve template, the least two additional leaflet portions comprise a septal leaflet portion and a posterior leaflet portion, and wherein the septal leaflet portion and the posterior leaflet portion have a height of 3A and the anterior leaflet portion has a height of 4A, where A is defined as ⅙ of a diameter of a valve annulus of the tricuspid valve.

10. The template of claim 9, further comprising another papillary muscle head portion formed at a commissure between at least three chordae portions extending from the septal leaflet portion or the posterior leaflet portion.

11. The template of claim 1, wherein the plurality of chordae portions have a longitudinal length of about 16 mm to about 22 mm.

12. The template of claim 1, wherein for a tricuspid valve template, chordae portions near an anteroposterior commissure side of the template are longer than chordae portions on an opposite side thereof.

13. The template of claim 1, further comprising a plurality of transverse chordae portions extending between the anterior leaflet portion and the at least two additional leaflet portions.

14. The template of claim 1, wherein the at least two additional leaflet portions comprise either (i) a posterior leaflet portion and a septal leaflet portion or (ii) two posterior leaflet portions.

* * * * *